(12) United States Patent
Zhao et al.

(10) Patent No.: US 10,441,519 B2
(45) Date of Patent: Oct. 15, 2019

(54) LOW VISCOSITY HAIR CARE COMPOSITION COMPRISING A BRANCHED ANIONIC/LINEAR ANIONIC SURFACTANT MIXTURE

(71) Applicant: The Procter & Gamble Company, Cincinnati, OH (US)

(72) Inventors: Jean Jianqun Zhao, Cincinnati, OH (US); Ioannis Constantine Constantinides, Wyoming, OH (US); Karl Shiqing Wei, Mason, OH (US); Peter Herbert Koenig, Montgomery, OH (US); Howard David Hutton, III, Oregonia, OH (US); Robert Wayne Glenn, Jr., Liberty Township, OH (US); Xiaoru Jenny Wang, Mason, OH (US); Brian Xiaoqing Song, Mason, OH (US); Edward Dewey Smith, III, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 15/789,208

(22) Filed: Oct. 20, 2017

(65) Prior Publication Data

US 2018/0110707 A1 Apr. 26, 2018

Related U.S. Application Data

(60) Provisional application No. 62/411,072, filed on Oct. 21, 2016.

(51) Int. Cl.
| | | |
|---|---|---|
| *C11D 1/12* | (2006.01) |
| *A61K 8/41* | (2006.01) |
| *A61K 8/04* | (2006.01) |
| *A61K 8/368* | (2006.01) |
| *A61K 8/46* | (2006.01) |
| *A61K 8/49* | (2006.01) |
| *A61Q 5/02* | (2006.01) |
| *A61Q 5/00* | (2006.01) |
| *A61Q 5/12* | (2006.01) |

(52) U.S. Cl.
CPC .............. *A61K 8/416* (2013.01); *A61K 8/046* (2013.01); *A61K 8/368* (2013.01); *A61K 8/463* (2013.01); *A61K 8/494* (2013.01); *A61K 8/4926* (2013.01); *A61Q 5/00* (2013.01); *A61Q 5/02* (2013.01); *A61Q 5/12* (2013.01); *A61K 2800/5424* (2013.01); *A61K 2800/5428* (2013.01); *A61K 2800/596* (2013.01)

(58) Field of Classification Search
CPC ......... C11D 1/12; C11D 3/0094; C11D 3/162; C11D 3/201; C11D 9/36
See application file for complete search history.

(56) References Cited

U.S. PATENT DOCUMENTS

| | | |
|---|---|---|
| 2,879,231 A | 3/1959 | Marshall |
| 3,709,437 A | 1/1973 | Wright |
| 3,950,532 A | 4/1976 | Bouillon et al. |
| 3,959,160 A | 5/1976 | Horsler et al. |
| 4,309,119 A | 1/1982 | Wittersheim |
| 4,329,334 A | 5/1982 | Su et al. |
| 4,839,166 A | 6/1989 | Grollier et al. |
| 4,867,971 A | 9/1989 | Ryan et al. |
| 5,294,644 A | 3/1994 | Login et al. |
| 5,332,569 A | 7/1994 | Wood et al. |
| 5,364,031 A | 11/1994 | Taniguchi et al. |
| 5,417,965 A | 5/1995 | Janchitraponvej et al. |
| 5,635,469 A | 6/1997 | Fowler et al. |
| 5,747,436 A | 5/1998 | Patel et al. |
| 5,776,444 A | 7/1998 | Birtwistle et al. |
| 5,816,446 A | 10/1998 | Steindorf et al. |
| 5,830,440 A | 11/1998 | Sturla et al. |
| 5,902,225 A | 5/1999 | Monson |
| 6,015,780 A | 1/2000 | Llosas Bigorra et al. |
| 6,020,303 A | 2/2000 | Cripe et al. |
| 6,039,933 A | 3/2000 | Samain et al. |
| 6,046,152 A | 4/2000 | Vinson et al. |
| 6,060,443 A | 5/2000 | Cripe et al. |
| 6,087,309 A | 7/2000 | Vinson et al. |
| 6,110,451 A | 8/2000 | Matz et al. |
| 6,133,222 A | 10/2000 | Vinson et al. |
| 6,153,569 A | 11/2000 | Halloran |
| 6,162,834 A | 12/2000 | Sebillotte-Arnaud et al. |

(Continued)

FOREIGN PATENT DOCUMENTS

| | | |
|---|---|---|
| CA | 2078375 A1 | 3/1994 |
| CN | 102697670 B | 7/2014 |

(Continued)

OTHER PUBLICATIONS

"Soda Shampoo", Mintel Database, Apr. 2015.
"Treatment Foam for Recurrent Scaling Conditions", Mintel Database, Aug. 2007.
All Final and Non-Final Office Actions for U.S. Appl. No. 15/135,657.
All Final and Non-Final Office Actions for U.S. Appl. No. 15/135,663.
All Final and Non-Final Office Actions for U.S. Appl. No. 15/135,677.
All Final and Non-Final Office Actions for U.S. Appl. No. 15/135,701.
All Final and Non-Final Office Actions for U.S. Appl. No. 15/135,998.
All Final and Non-Final Office Actions for U.S. Appl. No. 15/145,696.
All Final and Non-Final Office Actions for U.S. Appl. No. 15/2788,938.
All Final and Non-Final Office Actions for U.S. Appl. No. 15/299,860.

(Continued)

*Primary Examiner* — Charles I Boyer
(74) *Attorney, Agent, or Firm* — Angela K. Haughey

(57) ABSTRACT

The invention relates stable, low viscosity hair care compositions having high surfactant content comprising linear sulfates (with alkyl tail of C12 and above) and branched sulfates (with alkyl tail of C12 and above), a water-miscible solvent such as dipropylene glycol or glycerin. Suitable compositions have a ratio of (Linear anionic surfactant/Branched anionic surfactant)/Miscible solvent from about 0.2 to about 5 and a viscosity of less than about 500 cP at 26.5° C.

17 Claims, No Drawings

(56) References Cited

U.S. PATENT DOCUMENTS

| | | |
|---|---|---|
| 6,231,844 B1 | 5/2001 | Nambu |
| 6,268,431 B1 | 7/2001 | Snyder et al. |
| 6,284,225 B1 | 9/2001 | Bhatt |
| 6,329,331 B1 | 12/2001 | Aronson et al. |
| 6,335,312 B1 | 1/2002 | Coffindaffer et al. |
| 6,423,305 B1 | 7/2002 | Cauwet-Martin et al. |
| 6,451,300 B1 | 9/2002 | Dunlop et al. |
| 6,511,669 B1 | 1/2003 | Garnier et al. |
| 6,579,907 B1 | 6/2003 | Sebillotte-Arnaud et al. |
| 6,627,585 B1 | 9/2003 | Steer |
| 6,642,194 B2 | 11/2003 | Harrison |
| 6,649,155 B1 | 11/2003 | Dunlop et al. |
| 6,743,760 B1 | 6/2004 | Hardy et al. |
| 6,827,795 B1* | 12/2004 | Kasturi .................. A61K 8/44 134/39 |
| 6,992,054 B2 | 1/2006 | Lee et al. |
| 7,217,752 B2 | 5/2007 | Schmucker-Castner et al. |
| 7,220,408 B2 | 5/2007 | Decoster et al. |
| 7,223,385 B2 | 5/2007 | Gawtrey et al. |
| 7,485,289 B2 | 2/2009 | Gawtrey et al. |
| 7,504,094 B2 | 3/2009 | Decoster et al. |
| 7,531,497 B2 | 5/2009 | Midha et al. |
| 7,541,320 B2 | 6/2009 | Dabkowski et al. |
| 7,659,233 B2 | 2/2010 | Hurley et al. |
| 7,666,825 B2 | 2/2010 | Wagner et al. |
| 7,820,609 B2 | 10/2010 | Soffin et al. |
| 7,829,514 B2 | 11/2010 | Paul et al. |
| 7,928,053 B2 | 4/2011 | Hecht et al. |
| 7,977,288 B2 | 7/2011 | SenGupta |
| 8,084,407 B2 | 12/2011 | Soffin et al. |
| 8,088,721 B2 | 1/2012 | Soffin et al. |
| 8,124,063 B2 | 2/2012 | Harichian et al. |
| 8,300,949 B2 | 10/2012 | Xu |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,580,725 B2 | 11/2013 | Kuhlman et al. |
| 8,609,600 B2 | 12/2013 | Warr et al. |
| 8,628,760 B2 | 1/2014 | Carter et al. |
| 8,675,919 B2 | 3/2014 | Maladen |
| 8,680,035 B2 | 3/2014 | Kuhlman et al. |
| 8,699,751 B2 | 4/2014 | Maladen |
| 8,741,363 B2 | 6/2014 | Albrecht et al. |
| 8,771,765 B1 | 7/2014 | Fernandez |
| 8,795,635 B2 | 8/2014 | Tamarkin et al. |
| 8,883,698 B2 | 11/2014 | Scheibel et al. |
| 9,006,162 B1 | 4/2015 | Rizk |
| 9,186,642 B2 | 11/2015 | Dihora et al. |
| 9,265,727 B1 | 2/2016 | Lowenborg |
| 9,296,550 B2 | 3/2016 | Smith |
| 9,308,398 B2 | 4/2016 | Hutton et al. |
| 9,428,616 B2 | 8/2016 | Wagner |
| 9,512,275 B2 | 12/2016 | Wagner |
| 9,610,239 B2 | 4/2017 | Feng |
| 9,682,021 B2 | 6/2017 | Tamarkin et al. |
| 9,949,901 B2 | 4/2018 | Zhao et al. |
| 9,968,535 B2 | 5/2018 | Kitko |
| 9,993,420 B2 | 6/2018 | Glenn, Jr. et al. |
| 2001/0000467 A1 | 4/2001 | Murray |
| 2001/0006621 A1 | 7/2001 | Coupe et al. |
| 2001/0016565 A1 | 8/2001 | Bodet et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0059377 A1 | 3/2003 | Riley |
| 2003/0147842 A1 | 8/2003 | Restle et al. |
| 2003/0161802 A1 | 8/2003 | Flammer |
| 2003/0180246 A1 | 9/2003 | Frantz et al. |
| 2003/0185867 A1 | 10/2003 | Kerschner et al. |
| 2003/0223951 A1 | 12/2003 | Geary et al. |
| 2003/0228272 A1 | 12/2003 | Amjad et al. |
| 2004/0014879 A1 | 1/2004 | Denzer et al. |
| 2004/0235689 A1 | 11/2004 | Sakai et al. |
| 2005/0020468 A1 | 1/2005 | Frantz et al. |
| 2005/0136011 A1 | 6/2005 | Nekludoff |
| 2006/0002880 A1 | 1/2006 | Peffly |
| 2006/0057075 A1 | 3/2006 | Arkin et al. |
| 2006/0057097 A1 | 3/2006 | Derici |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0090777 A1* | 5/2006 | Hecht ................. C11D 17/0013 134/42 |
| 2006/0110415 A1 | 5/2006 | Gupta |
| 2006/0120982 A1 | 6/2006 | Derici et al. |
| 2006/0120988 A1 | 6/2006 | Bailey et al. |
| 2006/0183662 A1 | 8/2006 | Crotty et al. |
| 2006/0210139 A1 | 9/2006 | Carroll |
| 2006/0276357 A1 | 12/2006 | Smith, III et al. |
| 2007/0072781 A1 | 3/2007 | Soffin et al. |
| 2007/0154402 A1 | 7/2007 | Trumbore et al. |
| 2007/0155637 A1 | 7/2007 | Smith, III et al. |
| 2007/0179207 A1 | 8/2007 | Fernandez De Castro |
| 2007/0292380 A1 | 12/2007 | Staudigel et al. |
| 2008/0008668 A1 | 1/2008 | Harichian et al. |
| 2008/0152610 A1 | 6/2008 | Cajan |
| 2008/0206179 A1 | 8/2008 | Peffly et al. |
| 2008/0260655 A1 | 10/2008 | Tamarkin et al. |
| 2008/0261844 A1 | 10/2008 | Ruppert et al. |
| 2008/0317698 A1 | 12/2008 | Wells et al. |
| 2009/0029900 A1 | 1/2009 | Cetti et al. |
| 2009/0062406 A1 | 3/2009 | Loeffler |
| 2009/0155383 A1 | 6/2009 | Kitko et al. |
| 2009/0178210 A1 | 7/2009 | Bistram |
| 2009/0221463 A1 | 9/2009 | Kitko et al. |
| 2009/0312224 A1 | 12/2009 | Yang et al. |
| 2011/0008267 A1 | 1/2011 | Arkin et al. |
| 2011/0165107 A1 | 7/2011 | Derks et al. |
| 2011/0171155 A1* | 7/2011 | Federle ................. C12N 9/90 424/70.24 |
| 2011/0232668 A1 | 9/2011 | Hoffmann et al. |
| 2011/0269657 A1 | 11/2011 | Dihora et al. |
| 2011/0319790 A1 | 12/2011 | Kost et al. |
| 2012/0014901 A1 | 1/2012 | Sunkel et al. |
| 2012/0100091 A1 | 4/2012 | Hata et al. |
| 2012/0316095 A1 | 12/2012 | Wei et al. |
| 2013/0053295 A1 | 2/2013 | Kinoshita et al. |
| 2013/0053300 A1* | 2/2013 | Scheibel ................. A61K 8/342 510/536 |
| 2013/0115173 A1 | 5/2013 | Trumbore et al. |
| 2013/0143784 A1 | 6/2013 | Rizk |
| 2013/0156712 A1 | 6/2013 | Frantz |
| 2013/0189212 A1 | 7/2013 | Jawale et al. |
| 2013/0280192 A1 | 10/2013 | Carter et al. |
| 2013/0280202 A1 | 10/2013 | Stella et al. |
| 2013/0296289 A1* | 11/2013 | Hall ................. A61K 8/361 514/188 |
| 2014/0037703 A1 | 2/2014 | Dihora et al. |
| 2014/0039066 A1 | 2/2014 | Grimadell et al. |
| 2014/0131395 A1 | 5/2014 | Chang |
| 2014/0171471 A1 | 6/2014 | Krueger |
| 2014/0228268 A1 | 8/2014 | Fahl et al. |
| 2014/0237732 A1 | 8/2014 | Zuedel Fernandes et al. |
| 2014/0309154 A1 | 10/2014 | Carter et al. |
| 2014/0335041 A1 | 11/2014 | Peffly et al. |
| 2014/0348884 A1 | 11/2014 | Hilvert et al. |
| 2014/0348886 A1 | 11/2014 | Johnson et al. |
| 2015/0021496 A1 | 1/2015 | Shabbir |
| 2015/0050231 A1 | 2/2015 | Murase |
| 2015/0093420 A1 | 4/2015 | Snyder |
| 2015/0098921 A1 | 4/2015 | Franzke et al. |
| 2015/0218496 A1 | 8/2015 | Schmiedel et al. |
| 2015/0297489 A1 | 10/2015 | Kleinen et al. |
| 2015/0313818 A1 | 11/2015 | Stagg |
| 2015/0359725 A1 | 12/2015 | Glenn, Jr. et al. |
| 2016/0008257 A1 | 1/2016 | Zhou et al. |
| 2016/0113849 A1 | 4/2016 | Grimadell et al. |

(56) References Cited

U.S. PATENT DOCUMENTS

| | | |
|---|---|---|
| 2016/0128944 A1 | 5/2016 | Chawrai |
| 2016/0193125 A1 | 7/2016 | Jones et al. |
| 2016/0279048 A1 | 9/2016 | Jayaswal et al. |
| 2016/0303043 A1 | 10/2016 | Khoury |
| 2016/0309871 A1 | 10/2016 | Torres Rivera et al. |
| 2016/0310369 A1 | 10/2016 | Thompson et al. |
| 2016/0310370 A1 | 10/2016 | Zhao et al. |
| 2016/0310371 A1 | 10/2016 | Zhao |
| 2016/0310386 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao et al. |
| 2016/0354300 A1 | 12/2016 | Thompson et al. |
| 2017/0071837 A1 | 3/2017 | Schelges et al. |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0252273 A1 | 9/2017 | Renock et al. |
| 2017/0278249 A1 | 9/2017 | Stofel et al. |
| 2017/0304172 A1 | 10/2017 | Chang et al. |
| 2017/0304185 A1 | 10/2017 | Glenn, Jr. et al. |
| 2017/0333321 A1 | 11/2017 | Carnali |
| 2018/0057451 A1 | 3/2018 | Owens et al. |
| 2018/0110594 A1 | 4/2018 | Atkin |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera et al. |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110695 A1 | 4/2018 | Thompson et al. |
| 2018/0110696 A1 | 4/2018 | Johnson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |
| 2018/0110714 A1 | 4/2018 | Glenn, Jr. et al. |
| 2018/0116937 A1 | 5/2018 | Park et al. |
| 2018/0116941 A1 | 5/2018 | Wang |
| 2018/0221266 A1 | 8/2018 | Zhao et al. |
| 2018/0318194 A1 | 11/2018 | Hoffmann et al. |
| 2018/0344611 A1 | 12/2018 | Zhao et al. |
| 2018/0344613 A1 | 12/2018 | Zhao et al. |
| 2018/0344614 A1 | 12/2018 | Zhao et al. |
| 2019/0105242 A1 | 4/2019 | Song |
| 2019/0105243 A1 | 4/2019 | Song |
| 2019/0105244 A1 | 4/2019 | Song |
| 2019/0105245 A1 | 4/2019 | Song |
| 2019/0105246 A1 | 4/2019 | Cochran |
| 2019/0105247 A1 | 4/2019 | Song |
| 2019/0117543 A1 | 4/2019 | Zhao |
| 2019/0117544 A1 | 4/2019 | Zhao |
| 2019/0117545 A1 | 4/2019 | Zhao |

FOREIGN PATENT DOCUMENTS

| | | |
|---|---|---|
| CN | 105769617 A | 7/2016 |
| DE | 4315396 A1 | 11/1994 |
| DE | 202005009618 U1 | 9/2005 |
| DE | 102697668 B | 8/2013 |
| EP | 0574086 A2 | 12/1993 |
| EP | 1340485 A2 | 2/2003 |
| EP | 1346720 A2 | 9/2003 |
| EP | 1714678 A1 | 10/2006 |
| EP | 2042216 B1 | 9/2015 |
| JP | H08310924 A | 11/1996 |
| JP | 2964226 B2 | 10/1999 |
| JP | 3069802 B2 | 7/2000 |
| JP | 2002226889 A | 8/2002 |
| JP | 3634988 B2 | 3/2005 |
| JP | 3634991 B2 | 3/2005 |
| JP | 3634996 B2 | 3/2005 |
| JP | 2005187359 A | 7/2005 |
| JP | 5667790 B2 | 2/2015 |
| KR | 1020080111280 | 12/2008 |
| KR | 20140060882 A | 5/2014 |
| WO | WO199325650 A1 | 12/1993 |
| WO | WO9502389 A1 | 1/1995 |
| WO | WO9726854 A1 | 7/1997 |
| WO | WO9823258 A1 | 6/1998 |
| WO | WO9918928 A1 | 4/1999 |
| WO | WO9924004 A1 | 5/1999 |
| WO | WO0142409 A1 | 6/2001 |
| WO | WO0148021 A1 | 7/2001 |
| WO | WO2005023975 A1 | 3/2005 |
| WO | WO2009016555 A1 | 2/2009 |
| WO | WO2010052147 A2 | 5/2010 |
| WO | WO2012055587 A1 | 5/2012 |
| WO | WO2012084970 A1 | 6/2012 |
| WO | WO2013010706 A1 | 1/2013 |
| WO | WO2014148245 A1 | 9/2014 |
| WO | WO2016147196 A1 | 9/2016 |
| WO | WO2017207685 A1 | 12/2017 |
| WO | WO2018023180 A1 | 2/2018 |

OTHER PUBLICATIONS

All Final and Non-Final Office Actions for U.S. Appl. No. 15/481,777.
All Final and Non-Final Office Actions for U.S. Appl. No. 15/788,895.
All Final and Non-Final Office Actions for U.S. Appl. No. 15/788,949.
All Final and Non-Final Office Actions for U.S. Appl. No. 15/788,998.
All Final and Non-Final Office Actions for U.S. Appl. No. 15/789,010.
All Final and Non-Final Office Actions for U.S. Appl. No. 15/789,020.
All Final and Non-Final Office Actions for U.S. Appl. No. 15/789,030.
All Final and Non-Final Office Actions for U.S. Appl. No. 15/789,038.
All Final and Non-Final Office Actions for U.S. Appl. No. 15/789,044.
All Final and Non-Final Office Actions for U.S. Appl. No. 15/789,081.
All Final and Non-Final Office Actions for U.S. Appl. No. 15/789,172.
All Final and Non-Final Office Actions for U.S. Appl. No. 15/789,188.
All Final and Non-final Office Actions for U.S. Appl. No. 15/923,499.
All final and non-final office actions for U.S. Appl. No. 15/962,327.
All final and non-final office actions for U.S. Appl. No. 15/962,351.
All final and non-final office actions for U.S. Appl. No. 16/001,045.
All final and non-final office actions for U.S. Appl. No. 16/001,053.
All final and non-final office actions for U.S. Appl. No. 16/001,058.
All final and non-final office actions for U.S. Appl. No. 16/001,064.
PCT International Search Report and Written Opinion for PCT/US2016/028728 dated Aug. 5, 2016.
PCT International Search Report and Written Opinion for PCT/US2016/028729 dated Jun. 15, 2016.
PCT International Search Report and Written Opinion for PCT/US2016/028730 dated Aug. 5, 2016.
PCT International Search Report and Written Opinion for PCT/US2016/028735 dated Jul. 25, 2016.
PCT International Search Report and Written Opinion for PCT/US2016/028736 dated Jul. 25, 2016.
PCT International Search Report and Written Opinion for PCT/US2016/028742 dated Jul. 18, 2016.
PCT International Search Report and Written Opinion for PCT/US2016/058123 dated Dec. 21, 2016.
PCT International Search Report and Written Opinion for PCT/US2017/057486 dated Jan. 9, 2018.
PCT International Search Report and Written Opinion for PCT/US2017/057487 dated Dec. 19, 2017.
PCT International Search Report and Written Opinion for PCT/US2017/057488 dated Dec. 12, 2017.
PCT International Search Report and Written Opinion for PCT/US2017/057497 dated Jan. 8, 2018.
PCT International Search Report and Written Opinion for PCT/US2017/057503 dated Dec. 13, 2017.
PCT International Search Report and Written Opinion for PCT/US2017/057507 dated Dec. 13, 2017.
PCT International Search Report and Written Opinion for PCT/US2017/057510 dated Jan. 11, 2018.
PCT International Search Report and Written Opinion for PCT/US2017/057511 dated Feb. 2, 2018.

(56) References Cited

OTHER PUBLICATIONS

PCT International Search Report and Written Opinion for PCT/US2017/057514 dated Jan. 10, 2018.
PCT International Search Report and Written Opinion for PCT/US2017/057515 dated Dec. 11, 2017.
PCT International Search Report and Written Opinion for PCT/US2017/057522 dated Feb. 2, 2018.
PCT International Search Report and Written Opinion for PCT/US2017/057533 dated Jan. 8, 2018.
PCT International Search Report and Written Opinion for PCT/US2017/057541 dated Dec. 22, 2017.
U.S. Appl. No. 15/923,499, filed Mar. 16, 2018, Zhao et al.
U.S. Appl. No. 16/001,053, filed Jun. 6, 2018, Zhao et al.
U.S. Appl. No. 16/001,058, filed Jun. 6, 2018, Zhao et al.
U.S. Appl. No. 16/001,064, filed Jun. 6, 2018, Zhao et al.
U.S. Appl. No. 16/001,045, filed Jun. 6, 2018, Zhao et al.
U.S. Appl. No. 62/570,377, filed Oct. 10, 2017, Song et al.
U.S. Appl. No. 62/570,382, filed Oct. 10, 2017, Song et al.
U.S. Appl. No. 62/681,213, filed Jun. 6, 2018, Song et al.
U.S. Appl. No. 15/962,327, filed Apr. 25, 2018, Chang et al.
U.S. Appl. No. 15/962,351, filed Apr. 25, 2018, Chang et al.
U.S. Appl. No. 15/789,081, filed Oct. 20, 2017, Glenn, Jr. et al.
U.S. Appl. No. 15/789,172, filed Oct. 20, 2017, Zhao et al.
U.S. Appl. No. 15/789,188, filed Oct. 20, 2017, Zhao et al.
U.S. Appl. No. 16/156,606, filed Oct. 10, 2018, Cochran et al.
U.S. Appl. No. 16/156,072, filed Oct. 10, 2018, Song et al.
U.S. Appl. No. 16/156,015, filed Oct. 10, 2018, Song et al.
U.S. Appl. No. 16/156,038, filed Oct. 10, 2018, Song et al.
U.S. Appl. No. 16/156,045, filed Oct. 10, 2018, Song et al.
U.S. Appl. No. 16/156,053, filed Oct. 10, 2018, Song et al.
U.S. Appl. No. 16/170,516, filed Oct. 25, 2018, Chang et al.
U.S. Appl. No. 16/170,711, filed Oct. 25, 2018, Jamadagni et al.
U.S. Appl. No. 16/165,044, filed Oct. 25, 2018, Zhao et al.
U.S. Appl. No. 16/165,016, filed Oct. 19, 2018, Zhao et al.
U.S. Appl. No. 16/165,033, filed Oct. 19, 2018, Zhao et al.
All Final and Non-Final Office Actions for U.S. Appl. No. 16/156,045.
All final and non-final office actions for U.S. Appl. No. 15/379,660.
All final and non-final office actions for U.S. Appl. No. 15/379,674.
All final and non-final office actions for U.S. Appl. No. 15/448,911.
All final and non-final office actions for U.S. Appl. No. 15/467,317.
All Final and Non-Final Office Actions for U.S. Appl. No. 16/156,015.
All Final and Non-Final Office Actions for U.S. Appl. No. 16/156,038.
All Final and Non-Final Office Actions for U.S. Appl. No. 16/156,053.
All Final and Non-Final Office Actions for U.S. Appl. No. 16/156,066.
All Final and Non-Final Office Actions for U.S. Appl. No. 16/156,072.
All final and non-final office actions for U.S. Appl. No. 16/165,016.
All final and non-final office actions for U.S. Appl. No. 16/165,033.
All final and non-final office actions for U.S. Appl. No. 16/165,044.
All final and non-final office actions for U.S. Appl. No. 16/170,498.
All final and non-final office actions for U.S. Appl. No. 16/170,516.
All final and non-final office actions for U.S. Appl. No. 16/170,711.
Dehyquart Guar: Published Nov. 2010.
PCT International Search Report and Written Opinion for PCT/US2016/066752 dated Feb. 22, 2017.
PCT International Search Report and Written Opinion for PCT/US2016/066757 dated Feb. 22, 2017.
PCT International Search Report and Written Opinion for PCT/US2017/020604 dated May 11, 2017.
PCT International Search Report and Written Opinion for PCT/US2017/022737 dated Jun. 22, 2017.
PCT International Search Report and Written Opinion for PCT/US2018/029313 dated Jul. 11, 2018.
PCT International Search Report and Written Opinion for PCT/US2018/029315 dated Jun. 27, 2018.
PCT International Search Report and Written Opinion for PCT/US2018/036181 dated Aug. 3, 2018.
PCT International Search Report and Written Opinion for PCT/US2018/036185 dated Aug. 3, 2018.
Practical Modem Hair Science, Published 2012.
"Deep Image Matting", Ning Xu et al, Beckman Institute for Advanced Science and Technology, University of Illinois at Urbana-Champaign, Adobe Research, Mar. 10, 2017.
U.S. Appl. No. 16/248,900, filed Jan. 16, 2019, Torres Rivera et al.
U.S. Appl. No. 16/285,535, filed Feb. 26, 2019, Zhao et al.
U.S. Appl. No. 16/226,927, filed Dec. 20, 2018, Glenn, Jr. et al.
U.S. Appl. No. 16/226,914, filed Dec. 20, 2018, Gillis et al.
U.S. Appl. No. 16/376,033, filed Apr. 5, 2019, Zhao et al.
U.S. Appl. No. 16/390,270, filed Apr. 22, 2019, Torres Rivera et al.
"Natural Detangling Shampoo", Mintel Database, Sep. 13, 2017.
All final and non-final office actions for U.S. Appl. No. 16/226,914.
All final and non-final office actions for U.S. Appl. No. 16/226,927.
All final and non-final office actions for U.S. Appl. No. 16/248,900.
All final and non-final office actions for U.S. Appl. No. 16/285,535.
All final and non-final office actions for U.S. Appl. No. 16/376,033.
All final and non-final office actions for U.S. Appl. No. 16/390,270.
Anonymous: "Merquat Polyquaternium 47 Series, Water Soluble Polymers for Personal Care", Jul. 30, 2017, URL: https://www.in-cosmetics.com/_novadocuments/2729, retrieved on Dec. 21, 2018.
Carbopol Aqua SF-1 Polymer Technical Data Sheet, TDS-294, Dec. 2000.
Christensen et al., "Experimental Determination of Bubble Size Distribution in a Water Column by Interferometric Particle Imaging and Telecentric Direct Image Method", Student Report, Aalborg University, Jun. 3, 2014.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018, p. 1.
PCT International Search Report and Written Opinion for PCT/US2018/055102 dated Jan. 9, 2019.
PCT International Search Report and Written Opinion for PCT/US2018/055103 dated Jan. 9, 2019.
PCT International Search Report and Written Opinion for PCT/US2018/055104 dated Jan. 18, 2019.
PCT International Search Report and Written Opinion for PCT/US2018/055105 dated Jan. 8, 2019.
PCT International Search Report and Written Opinion for PCT/US2018/055106 dated Jan. 16, 2019.
PCT International Search Report and Written Opinion for PCT/US2018/055107 dated Jan. 28, 2019.
PCT International Search Report and Written Opinion for PCT/US2018/056669 dated Jan. 31, 2019.
PCT International Search Report and Written Opinion for PCT/US2018/056673 dated Feb. 5, 2019.
PCT International Search Report and Written Opinion for PCT/US2018/056674 dated Feb. 5, 2019.
PCT International Search Report and Written Opinion for PCT/US2018/057451 dated Feb. 25, 2019.
PCT International Search Report and Written Opinion for PCT/US2018/057476 dated Jan. 18, 2019.
PCT International Search Report and Written Opinion for PCT/US2018/066697 dated Mar. 15, 2019.
PCT International Search Report and Written Opinion for PCT/US2018/066701 dated Mar. 15, 2019.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-theSafety-Assessment-of-Polyquaternium-10.pdf, retrieved on Dec. 20, 2018.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, Nov. 1, 2008, pp. 304-308, p. 305—left-hand column.

\* cited by examiner

LOW VISCOSITY HAIR CARE COMPOSITION COMPRISING A BRANCHED ANIONIC/LINEAR ANIONIC SURFACTANT MIXTURE

FIELD OF THE INVENTION

The invention relates to a concentrated, low viscosity hair care composition that is stable and can also be delivered to the hair in various forms including a foamed form.

BACKGROUND OF THE INVENTION

Described herein is a concentrated, low viscosity hair care composition that is stable and can also be delivered to the hair in various forms including a foamed form. Delivery of cleansing composition in the form of foam is desirable to the consumer. The low density of the foam necessitates a high surfactant composition in order for the consumer to receive the appropriate level of cleansing in a realistic product volume in one dose. However, typically, high surfactant liquid cleansing composition exhibit high viscosity, which makes it difficult to deliver via a pump foam dispenser, a squeeze foam dispenser or an aerosol foam dispenser. Therefore, delivery as a foam is facilitated by low viscosity compositions that contain a high concentration of cleansing surfactants.

Mechanical or pump foams for the personal cleansing category represent an attractive form to the consumers. A hair care product delivered via foam is readily spread on hair and enables hair cleansing without leaving significant residue on hair because the structuring effect of foam enables the use of compositions without polymeric or waxy structurants. Because of the low density of the foam, high concentration of surfactant is required to deliver sufficient amount of detersive surfactant for each use. However, high surfactant liquid cleansing compositions often exhibit high viscosity, which makes it difficult to deliver with a typical pump foam dispenser. High surfactant liquid cleansing compositions can become unstable and phase separate. Based on the foregoing, there is a need for a low viscosity, stable, concentrated liquid cleansing composition for delivery as foam. In addition, the combination of clear product in a clear container is visually appealing. Thus, there is a need for developing transparent or translucent compositions. High content surfactant compositions may be prepared by using surfactants that have tails with short alkyl chains (10 to 11 carbon atoms). This approach can result in a less mild composition. Thus, there is a need to prepare mild surfactant compositions having low content of surfactants with a tail having an alkyl chain with 10 or 11 (or lower) carbon atoms.

It has been surprisingly found that clear, stable, low viscosity compositions having high surfactant content can be prepared by using linear sulfates (with alkyl tail of 12 carbon atoms or above) and branched sulfates (with alkyl tail of 12 carbon atoms or above), a water-miscible solvent such as dipropylene glycol or glycerin. Suitable compositions have a ratio of (Linear anionic surfactant/Branched anionic surfactant)/Miscible solvent lower than about 0.2 and a ratio of (Branched anionic surfactant/Miscible solvent) lower than about 5.

SUMMARY OF THE INVENTION

The invention relates to a stable concentrated hair care composition comprising from about 20 weight % to about 45 weight % total surfactant; from about 6 weight % to about 30 weight % branched anionic surfactant with tail having an alkyl chain with 12 to 18 carbon atoms; from about 0.1% weight % to about 20 weight % linear anionic surfactant with tail having an alkyl chain with 12 to 18 carbon atoms; from about 2 weight % to about 12 weight % water-miscible solvent; and from about 35 weight % to about 78 weight % of water; wherein the concentrated hair care has Ratio of (Linear anionic surfactant/Branched anionic surfactant)/Miscible solvent of less than about 0.2; and wherein the ratio of branched anionic surfactant/miscible solvent is less than about 5; and wherein the concentrated hair care has a viscosity of less than 500 cP at 26.5° C.

The invention also relates to a stable concentrated hair care composition comprising from about 20 weight % to about 45 weight % total surfactant; from about 6 weight % to about 30 weight % branched anionic surfactant with tail having an alkyl chain with 12 to 18 carbon atoms; from about 2 weight % to about 12 weight % water-miscible solvent; and from about 35 weight % to about 78 weight % of water; and wherein the ratio of (Linear anionic surfactant/Branched anionic surfactant)/Miscible solvent is less than about 0.2; and wherein the ratio of branched anionic surfactant/miscible solvent is less than about 5; and wherein the concentrated hair care composition has a viscosity of less than 500 cP at 26.5° C.; and wherein the composition has about 0 weight % linear anionic surfactant with tail having an alkyl chain with 12 to 18 carbon atoms.

DETAILED DESCRIPTION OF THE INVENTION

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "M.Wt." refers to the weight average molecular weight unless otherwise stated. Molecular weight is measured using industry standard method, gel permeation chromatography ("GPC").

As used herein, "personal care compositions" includes products such as shampoos, shower gels, liquid hand cleansers, hair colorants, facial cleansers, laundry detergent, dish detergent, and other surfactant-based liquid compositions As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The hair care compositions described herein are stable, and have low viscosity while also having high surfactant content. The surfactant system comprises linear sulfates (with alkyl tail of 12 carbon atoms or above) and branched sulfates (with alkyl tail of 12 carbon atoms or above), a water-miscible solvent including, but not limited to dipropylene glycol and/or glycerin. Suitable compositions have a ratio of (Linear anionic surfactant/branched anionic surfactant)/miscible solvent lower than about 0.2 and a ratio of (branched anionic surfactant/miscible solvent) lower than about 5. The hair care compositions can be shampoo. The hair care compositions can be clear, and they can be concentrated and/or compact formulations.

A. Surfactants

The hair care composition can comprise a total surfactant level of from about 20% to about 45% by weight, from about 25% to about 45% by weight, from about 25% to about 40% by weight, from about 30% to about 40% by weigh, from about 30% to about 35% by weight. The total surfactants can include, but are not limited to, amphoteric, branched anionic surfactants, linear anionic surfactants and combinations thereof.

1. Branched Anionic Surfactant

The hair care composition can comprise from about 6% to about 30% by weight, from about 6 to about 28% by weight, from about 6% to about 24% by weight, and from about 8% to about 24% by weight of branched anionic surfactant, with a tail having an alkyl chain with 12 carbon atoms or higher, alternatively about 12 to about 18 carbon atoms.

Suitable branched anionic surfactant, with a tail having an alkyl chain with 12 carbon atoms or higher, include, but are not limited to the following surfactants: sodium trideceth sulfate, sodium tridecyl sulfate, sodium C12-13 alkyl sulfate, sodium C12-15 alkyl sulfate, sodium C12-18 alkyl sulfate, sodium C12-13 pareth sulfate, sodium C12-13 pareth-n sulfate, sodium C12-14 pareth-n sulfate, and combinations thereof. Other salts of all the aforementioned surfactants are useful, such as TEA, DEA, ammonia, potassium salts. Useful alkoxylates include the ethylene oxide, propylene oxide and EO/PO mixed alkoxylates. Phosphates, carboxylates and sulfonates prepared from branched alcohols are also useful anionic branched surfactants. Branched surfactants can be derived from synthetic alcohols such as the primary alcohols from the liquid hydrocarbons produced by Fischer-Tropsch condensed syngas, for example Safol™ 23 Alcohol available from Sasol North America, Houston, Tex.; from synthetic alcohols such as Neodol™ 23 Alcohol available from Shell Chemicals, USA; from synthetically made alcohols such as those described in U.S. Pat. No. 6,335,312 issued to Coffindaffer, et al on Jan. 1, 2002. Suitable examples of alcohols are Safol™ 23 and Neodol™ 23. Suitable examples of alkoxylated alcohols are Safol™ 23-3 and Neodol™ 23-3. Another suitable example is Exaal-13 from ExxonMobil North America. Sulfates can be prepared by conventional processes to high purity from a sulfur based SO3air stream process, chlorosulfonic acid process, sulfuric acid process, or Oleum process. Preparation via air stream in a falling film reactor is a preferred sulfation process. The anionic surfactant may also be STnS, wherein n can define average moles of ethoxylation. n can range from about 0 to about 3.5, from about 0.5 to about 3.5, from about 1.1 to about 2.5, from about 1.8 to about 2.2, or n can be about 2.

2. Linear Anionic Surfactant

The hair care composition can comprise from about 0% to about 20% by weight, from about 1% to about 20% by weight, from about 2% to about 20% by weight, from about 3% to about 20% by weight, and from about 4% to about 15% by weight, of linear anionic surfactant with a tail having an alkyl chain with 12 carbon atoms or higher, alternatively from about 12 to about 18 carbon atoms.

Suitable anionic detersive surfactant components for use in the composition herein include those which are known for use in hair care or other personal care shampoo compositions. The anionic detersive surfactant may be a combination of sodium lauryl sulfate and sodium laureth-n sulfate. Alternatively, the anionic detersive surfactant can be sodium laureth sulfate with an average of one mole ethoxylate. The concentration of the anionic surfactant component in the composition should be sufficient to provide the desired cleaning and lather performance.

Anionic surfactants suitable for use herein include alkyl sulfates and alkyl ether sulfates of the formula $ROSO_3M$ and $RO(C_2H_4O)_xSO_3M$, wherein R is alkyl or alkenyl of from about 8 to about 18 carbon atoms, x is 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats such as coconut oil, palm oil, palm kernel oil, or tallow, or can be synthetic.

TABLE 1

Examples of Typical Alkyl Sulfates and Alky Ether Sulfates

| Surfactant | Supplier | Activity | SLS | SLE1S | SLE2S | SLE3S | SLE > 3S |
|---|---|---|---|---|---|---|---|
| Sodium Lauryl Sulfate | Stepan STEOL SLS | 29% by weight | 100 | 0 | 0 | 0 | 0 |
| Sodium Laureth-1 Sulfate | Stepan STEOL SLES-1 | 26% by weight | 45.5 | 26.3 | 11.8 | 0.07 | 16.33 |
| Sodium Laureth-3 Sulfate | Stepan STEOL SLES-3 | 28% by weight | 18 | 16.7 | 12.6 | 12.4 | 40.30 |

Some non-limiting examples of linear surfactants are:

Alkyl Sulfates

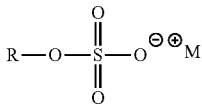

Alkyl sulfates where R is $C_{12}$-$C_{18}$ alkyl (linear, saturated or unsaturated) or mixtures thereof and $M^+$ is monovalent cation. Examples include sodium lauryl sulfate (where R is $C_{12}$ alkyl and $M^+$ is $Na^+$), ammonium lauryl sulfate (where R is $C_{12}$ alkyl and $M^+$ is $NH_3^+$), and sodium cocosulfate (where R is coconut alkyl and $M^+$ is $Na^+$);

Alkyl Ether Sulfates

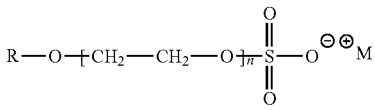

Alkyl ether sulfates where R is $C_{12}$-$C_{18}$ alkyl (linear, saturated or unsaturated) or mixtures thereof, n=1-12, and $M^+$ is monovalent cation. Examples include sodium laureth sulfate (where R is $C_{12}$ alkyl and $M^+$ is $Na^+$, n=1-3), ammonium laureth sulfate (where R is $C_{12}$ alkyl, $M^+$ is $NH_3^+$, n=1-3), and Sodium trideceth sulfate (where R is $C_{13}$ alkyl, $M^+$ is $Na^+$, and n=1-4);

Some non-limiting examples of sulfonate surfactants are:

Alkyl glyceryl ether sulfonates:

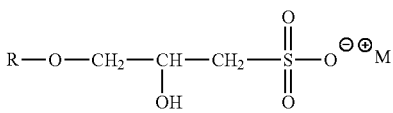

where R=$C_{12}$-$C_{18}$ alkyl (linear, saturated or unsaturated) or mixtures thereof and $M^+$=monovalent cation, such as Sodium Cocoglyceryl Ether Sulfonate (R=coco alkyl, $M^+$=$Na^+$);

Alpha olefin sulfonates prepared by sulfonation of long chain alpha olefins. Alpha olefin sulfonates consist of mixtures of alkene sulfonates,

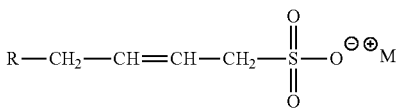

where R=$C_8$-$C_{18}$ alkyl or mixtures thereof and $M^+$=monovalent cation;

Hydroxyalkyl sulfonates,

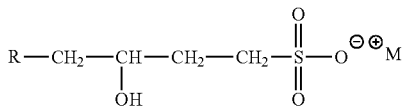

where R=$C_8$-$C_{18}$ alkyl or mixtures thereof and $M^+$=monovalent cation. Examples include Sodium C12-14 Olefin Sulfonate (R=$C_8$-$C_{10}$ alkyl, $M^+$=$Na^+$) and Sodium C 14-16 Olefin Sulfonate (R=$C_{10}$-$C_{12}$ alkyl, $M^+$=$Na^+$).

Examples of additional anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth-1 sulfate, sulfate, sodium trideceth-2 sulfate, sulfate, sodium trideceth-3 sulfate, sodium tridecyl sulfate, sodium methyl lauroyl taurate, sodium methyl cocoyl taurate, sodium lauroyl isethionate, sodium cocoyl isethionate, sodium laureth-sulfosuccinate, sodium laurylsulfosuccinate, sodium tridecyl benzene sulfonate, sodium dodecyl benzene sulfonate, and mixtures thereof.

Additional anionic surfactants suitable for use herein include, but not limited to, acyl isethionate, acyl methyl isethionate, acyl glutamate, acyl glycinate, acyl sarcosinate, acyl alaninate, acyl taurate, sulfosuccinate, alkyl benzene sulfonate, alkyl ether carboxylate, alkylamphoacetate, alpha olefin sulfonate, and mixtures thereof. Examples of such suitable anionic surfactants include, but not limited to, sodium cocoyl isethionate, sodium lauroyl isethionate, sodium lauroyl methyl isethionate, sodium cocoyl glutamate, disodium cocoyl glutamate, sodium lauroyl glutamate, disodium lauroyl glutamate, sodium cocoyl alaninate, sodium lauroyl alaninate, sodium lauroyl glycinate, sodium cocoyl glycinate, sodium laureth sulfosuccinate, disodium laureth sulfosuccinate, sodium lauryl sulfosuccinate, disodium lauryl sulfosuccinate, sodium lauryl glucose carboxylate, sodium cocoyl glucose carboxylate, sodium cocoyl amphoacetate, sodium lauroyl amphoacetate, sodium methyl cocoyl taurate, and mixtures thereof.

3. Co-Surfactant

The hair care composition can comprise from about 0% % to about 10% by weight, from about 0.5 to about 10% by weight, from about 1% to about 8% by weight, and from about 2% to about 8% by weight of one or more co-surfactants selected from the group consisting of amphoteric surfactant, zwitterionic surfactant, non-ionic surfactant and mixtures thereof. Various examples and descriptions of detersive surfactants are set forth in U.S. Pat. No. 8,440,605; U.S. Patent Application Publication No. 2009/155383; and U.S. Patent Application Publication No. 2009/0221463, which are incorporated herein by reference in their entirety.

Amphoteric detersive surfactants suitable for use in the hair care composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present hair care composition include sodium cocoamphoacetate, sodium cocoamphodiacetate, sodium lauroamphoacetate, disodium lauroamphodiacetate, sodium cocaminopropionate, sodium cocaminodipropionate, sodium cocoamphohydroxypropylsulfonate, sodium cocoamphopropionate, sodium cornamphopropionate, sodium lauraminopropionate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium caprylo-amphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof. Also suitable amphoteric surfactants include amidobetaines and amidosulfobetaines, wherein the RCONH(CH$_2$)$_3$ radical, wherein R is a C$_{11}$-C$_{17}$ alkyl, is attached to the nitrogen atom of the betaine are also useful in this invention.

Suitable non-ionic surfactants can be selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide. PEG-5 Lauramide, PEG-3 Oleamide. PPG-2 Cocamide, PPG-2 Hydroxyethyl Cocamide, and mixtures thereof.

Suitable nonionic surfactants for use include those described in McCutcheon's Detergents and Emulsifiers, North American edition (1986), Allured Publishing Corp., and McCutcheon's Functional Materials, North American edition (1992). Suitable nonionic surfactants for use in the hair care compositions include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones B. Water Miscible Solvent The hair care composition comprises water-miscible solvent or combination of water-miscible solvent. The content of the water-miscible solvent is from about 2 wt % to about 12 wt %, from about 3 wt % to about 10 wt %, from about 4 wt % to about 8 wt %. Suitable water miscible solvents include, but are not limited to, dipropylene glycol, tripropylene glycol, diethylene glycol, ethylene glycol, propylene glycol, glycerin, 1,3-propane diol, 2,2-propanediol, 1,2-butanediol, 1,3-butanediol, 1,4-butanediol, 2,3-butanediol, 2-methyl-2,4-pentanediol, and mixtures thereof. The hair care composition may comprise two or more water miscible solvents, wherein at least one of the solvents is dipropylene glycol.

The hair care compositions may have a pH in the range from about 2 to about 10, at 25° C. Alternatively, the hair care composition has a pH in the range from about 4 to about 7, which may help to solubilize minerals and redox metals already deposited on the hair. Thus, the hair care composition can also be effective toward washing out the existing minerals and redox metals deposits, which can reduce cuticle distortion and thereby reduce cuticle chipping and damage.

The hair care composition can also comprise a hydrotope or mixture of hydrotrope. Suitable hydrotrope include, but are not limited to alkali metal or ammonium salt of a lower alkyl benzene sulphonates such as Sodium Xylene Sulfonate (SXS), sodium cumene sulphonate, sodium toluene sulphonate and mixtures thereof.

C. Water Carrier

The compositions can include from about 35% to about 78% by weight, from about 40% to about 78% by weight, from about 45% to about 78% by weight, from about 50% to about 75%, from about 55% to about 70% water, from about 60% to about 68% by weight of water.

D. Cationic Polymers

The hair care composition also comprises a cationic polymer. These cationic polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic polymer can be a mixture of cationic polymers.

The hair care composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

According to one embodiment, the cationic polymer, including but not limited to a cationic guar polymer, has a molecular weight of less than 1.0 million g/mol, or from about 10 thousand to about 1 million g/mol, or from about 25 thousand to about 1 million g/mol, or from about 50 thousand to about 1 million g/mol, or from about 100 thousand to about 1 million g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.7 meq/g.

According to one embodiment, the cationic guar polymer has a weight average molecular weight of less than about 1.0 million g/mol, and has a charge density of from about 0.1 meq/g to about 2.5 meq/g. In an embodiment, the cationic guar polymer has a weight average molecular weight of less than 950 thousand g/mol, or from about 10 thousand to about 900 thousand g/mol, or from about 25 thousand to about 900 thousand g/mol, or from about 50 thousand to about 900 thousand g/mol, or from about 100 thousand to about 900 thousand g/mol. from about 150 thousand to about 800 thousand g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.5 meq/g.

The hair care composition can comprise from about 0.05% to less than about 1%, from about 0.05% to about 0.9%, from about 0.1% to about 0.8%, or from about 0.2% to about 0.7% of cationic polymer (a), by total weight of the composition.

The cationic guar polymer may be formed from quaternary ammonium compounds. In an embodiment, the quaternary ammonium compounds for forming the cationic guar polymer conform to the general formula 1:

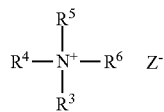

wherein where $R^3$, $R^4$ and $R^5$ are methyl or ethyl groups; $R^6$ is either an epoxyalkyl group of the general formula 2:

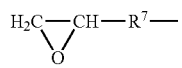

or $R^6$ is a halohydrin group of the general formula 3:

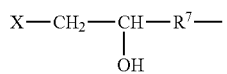

wherein $R^7$ is a $C_1$ to $C_3$ alkylene; X is chlorine or bromine, and Z is an anion such as Cl—, Br—, I—S or $HSO_4$—.

In an embodiment, the cationic guar polymer conforms to the general formula 4:

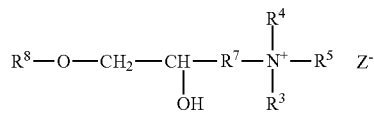

wherein $R^8$ is guar gum; and wherein $R^4$, $R^5$, $R^6$ and $R^7$ are as defined above; and wherein Z is a halogen. In an embodiment, the cationic guar polymer conforms to Formula 5:

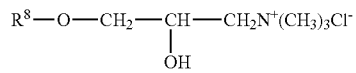

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a molecular weight of 500,000 g/mol. Other suitable guar hydroxypropyltrimonium chloride are: guar hydroxypropyltrimonium chloride which has a charge density of about 1.1 meq/g and a molecular weight of about 500,000 g/mol is available from ASI, a charge density of about 1.5 meq/g and a molecular weight of about 500,000 g/mole is available from ASI. Other suitable guar hydroxypropyltrimonium chloride are: Hi-Care 1000, which has a charge density of about 0.7 meq/g and a Molecular weight of about 600,000 g/mole and is available from Rhodia; N-Hance 3269 and N-Hance 3270, which has a charge density of about 0.7 meq/g and a molecular weight of about 425,000 g/mol and is available from ASIAquaCat CG518 has a charge density of about 0.9 meq/g and a Molecular weight of about 50,000 g/mol and is available from ASI. BF-13, which is a borate (boron) free guar of charge density of about 1.1 meq/g and molecular weight of about 800,000 and BF-17, which is a borate (boron) free guar of charge density of about 1.7 meq/g and M. W.t of about 800,000 both available from ASI.

The hair care compositions may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and also is affected by climate. Non Guar Galactomannan polymer derivatives suitable for use can have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and Cassia gum (5 parts mannose/1 part galactose).

In one embodiment of the invention, the non-guar galactomannan polymer derivatives have a M. Wt. from about 1,000 to about 1,000,000, and/or form about 5,000 to about 900,000.

The hair care compositions of the can also include galactomannan polymer derivatives which have a cationic charge density from about 0.5 meq/g to about 7 meq/g. The galactomannan polymer derivatives can have a cationic charge density from about 1 meq/g to about 5 meq/g. The degree of substitution of the cationic groups onto the galactomannan structure should be sufficient to provide the requisite cationic charge density.

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

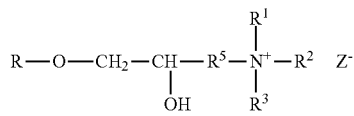

wherein R is the gum. The cationic galactomannan derivative can be a gum hydroxypropyltrimethylammonium chloride, which can be more specifically represented by the general formula 7:

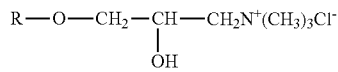

Alternatively the galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose is greater than about 4:1, a molecular weight of about 50,000 g/mol to about 1,000,000 g/mol, and/or from about 100,000 g/mol to about 900,000 g/mol and a cationic charge density from about 1 meq/g to about 5 meq/g, and/or from 2 meq/g to about 4 meq/g and can also be derived from a cassia plant.

The hair care compositions can comprise at least about 0.05% of a galactomannan polymer derivative by weight of the composition, alternatively from about 0.05% to about 2%, by weight of the composition, of a galactomannan polymer derivative.

The hair care compositions can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The hair care compositions can comprise cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers for use in the hair care compositions can have a molecular weight about 50,000 g/mol to about 1,000,000 g/mol and/or from about 100,000 g/mol to about 1,000,000 g/mol.

The hair care compositions can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

The cationically modified starch polymers can be selected from degraded cationic maize starch, cationic tapioca, cationic potato starch, and mixtures thereof. Alternatively, the cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in hair care compositions are available from known starch suppliers. Also suitable for use in hair care compositions are nonionic modified starch that can be further derivatized to a cationically modified starch as is known in the art. Other suitable modified starch starting materials may be quaternized, as is known in the art, to produce the cationically modified starch polymer suitable for use in hair care compositions.

Starch Degradation Procedure: a starch slurry can be prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

The hair care composition can comprise a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

The cationic copolymer can comprise:
(i) an acrylamide monomer of the following Formula AM:

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and
(ii) a cationic monomer conforming to Formula CM:

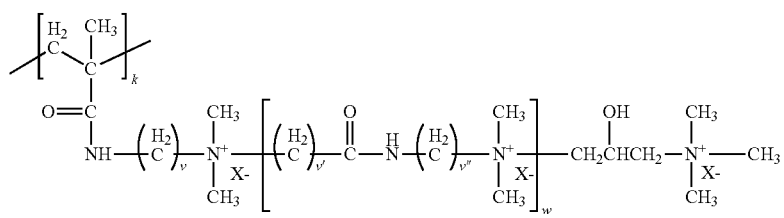

Formula CM where k=1, each of v, v', and v" is independently an integer of from 1 to 6, w is zero or an integer of from 1 to 10, and $X^-$ is an anion.

The cationic monomer can conform to Formula CM and where k=1, v=3 and w=0, z=1 and $X^-$ is $Cl^-$ to form the following structure:

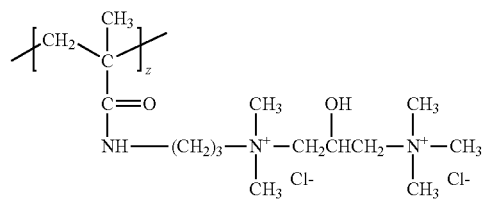

The above structure may be referred to as diquat. Alternatively, the cationic monomer can conform to Formula CM and wherein v and v" are each 3, v'=1, w=1, y=1 and $X^-$ is $Cl^-$, such as:

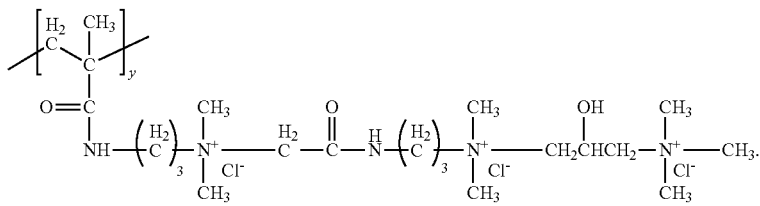

The above structure may be referred to as triquat.

Suitable acrylamide monomer include, but are not limited to, either acrylamide or methacrylamide.

In an alternative embodiment, the cationic copolymer is of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can comprise a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. In an embodiment, cationized esters of the (meth)acrylic acid containing a quaternized N atom are quaternized dialkylaminoalkyl (meth)acrylates with C1 to C3 in the alkyl and alkylene groups. Suitable cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. In an embodiment, the cationized esters of the (meth)acrylic acid containing a quaternized N atom is dimethylaminoethyl acrylate, which is quaternized with an alkyl halide, or with methyl chloride or benzyl chloride or dimethyl sulfate (ADAME-Quat). The cationic monomer when based on (meth)acrylamides can be quaternized dialkylaminoalkyl (meth)acrylamides with C1 to C3 in the alkyl and alkylene groups, or dimethylaminopropylacrylamide, which is quaternized with an alkyl halide, or methyl chloride or benzyl chloride or dimethyl sulfate.

Suitable cationic monomer based on a (meth)acrylamide include quaternized dialkylaminoalkyl(meth)acrylamide with C1 to C3 in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

The cationic copolymer can have a molecular weight from about 10 thousand g/mol to about 1 million g/mol, or from about 25 thousand g/mol to about 1 million g/mol, or from about 50 thousand g/mol to about 1 million g/mol, or from about 100 thousand g/mol to about 1.0 million g/mol, or from about 150 thousand g/mol to about 1.0 million g/mol.

(a) Cationic Synthetic Polymers

The hair care composition can comprise a cationic synthetic polymer that may be formed from i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers having the following structure:

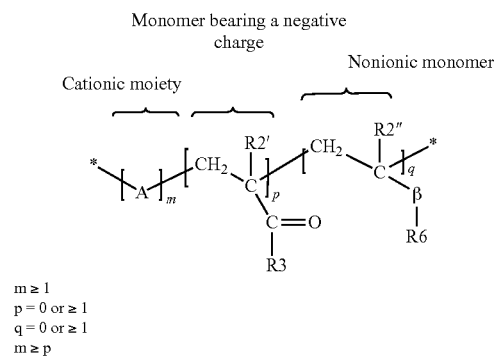

Monomer bearing a negative charge
Cationic moiety
Nonionic monomer $m \geq 1$
$p = 0$ or $\geq 1$
$q = 0$ or $\geq 1$
$m \geq p$ where A, may be one or more of the following cationic moieties:

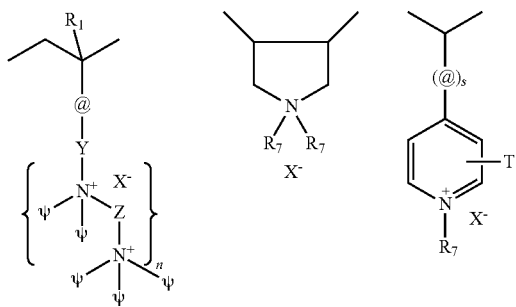

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;
where Z=C1-C22 alkyl, alkyloxy, aryl or aryloxy;
where R1=H, C1-C4 linear or branched alkyl;
where s=0 or 1, n=0 or≥1;
where T and R7=C1-C22 alkyl; and
where X—=halogen, hydroxide, alkoxide, sulfate or alkyl-sulfate.

Where the monomer bearing a negative charge is defined by R2'=H, C1-C4 linear or branched alkyl and R3 as:

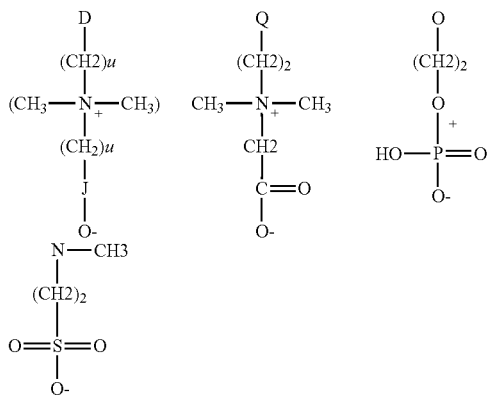

where D=O, N, or S;
where Q=NH$_2$ or 0;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

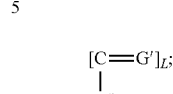

and
where G' and G" are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyl-dialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula —NR$_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropane-sulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth)acrylic acid), monoalkylesters of alpha ethylenically unsaturated dicarboxylic acids, monoalkylamides of alpha ethylenic ally unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X—) in association with the synthetic cationic polymers may be any known counterion so long as the polymers remain soluble or dispersible in water, in the hair care composition, or in a coacervate phase of the hair care composition, and so long as the counterions are physically and chemically compatible with the essential components of the hair care composition or do not otherwise unduly impair product performance, stability or aesthetics. Non limiting examples of such counterions include halides (e.g., chlorine, fluorine, bromine, iodine), sulfate and methylsulfate.

The concentration of the cationic polymers ranges about 0.025% to about 5%, from about 0.1% to about 3%, and/or from about 0.2% to about 1%, by weight of the hair care composition.

Suitable cationic cellulose polymers are salts of hydroxyethyl cellulose reacted with trimethyl ammonium substituted epoxide, referred to in the industry (CTFA) as Polyquaternium 10 and available from Dow/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

E. Conditioning Agents

The hair care compositions may comprise one or more conditioning agent. Conditioning agents include materials that are used to give a particular conditioning benefit to hair and/or skin. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

1. Silicone Conditioning Agents

The hair care composition can comprise from about 0% to about 20% by weight, alternatively from about 6% to about 18% by weight; and alternatively from about 8% to about 16% by weight of one of more silicones with a particle size of less than about 300 nm, alternatively less than about 200 nm, and alternatively less than about 100 nm. The silicone can be in the form of a nanoemulsion.

The particle size of the one or more silicones may be measured by dynamic light scattering (DLS). A Malvern Zetasizer Nano ZEN3600 system (www.malvern.com) using He—Ne laser 633 nm may be used for the measurement at 25° C.

The autocorrelation function may be analyzed using the Zetasizer Software provided by Malvern Instruments, which determines the effective hydrodynamic radius, using the Stokes-Einstein equation:

$$D = \frac{k_B T}{6\pi\eta R}$$

wherein $k_B$ is the Boltzmann Constant, T is the absolute temperature, $\eta$ is the viscosity of the medium, D is the mean diffusion coefficient of the scattering species, and R is the hydrodynamic radius of particles.

Particle size (i.e. hydrodynamic radius) may be obtained by correlating the observed speckle pattern that arises due to Brownian motion and solving the Stokes-Einstein equation, which relates the particle size to the measured diffusion constant, as is known in the art.

For each sample, 3 measurements may be made and Z-average values may be reported as the particle size.

In an embodiment, the one or more silicones may be in the form of a nanoemulsion. The nanoemulsion may comprise any silicone suitable for application to the skin and/or hair.

In an embodiment, the one or more silicones may include in their molecular structure polar functional groups such as Si—OH (present in dimethiconols), primary amines, secondary amines, tertiary amines, and quaternary ammonium salts. The one or more silicones may be selected from the group consisting of aminosilicones, pendant quaternary ammonium silicones, terminal quaternary ammonium silicones, amino polyalkylene oxide silicones, quaternary ammonium polyalkylene oxide silicones, and amino morpholino silicones.

The one or more silicones may comprise:

(a) at least one aminosilicone corresponding to formula (V):

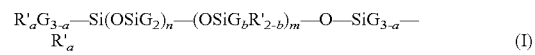
(I)

in which:

G is chosen from a hydrogen atom, a phenyl group, OH group, and $C_1$-$C_8$ alkyl groups, for example methyl, a is an integer ranging from 0 to 3, and in one embodiment a is 0, b is chosen from 0 and 1, and in one embodiment b is 1, m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10;

R' is a monovalent group of formula —$C_qH_{2q}L$ in which q is a number from 2 to 8 and L is an optionally quaternized amine group chosen from the groups:

—NR''—$CH_2$—$CH_2$—N'($R^1$)$_2$,

—N(R'')$_2$,

—$N^+$(R'')$_3$$A^-$,

—$N^+$H(R'')$_2$$A^-$,

—$N^+$$H_2$(R'')$A^-$, and

—N(R'')—$CH_2$—$CH_2$—$N^+$R''$H_2$$A^-$, in which R'' can be chosen from a hydrogen atom, phenyl groups, benzyl groups, and saturated monovalent hydrocarbon-based groups, such as for example an alkyl group comprising from 1 to 20 carbon atoms, and $A^-$ is chosen from halide ions such as, for example, fluoride, chloride, bromide and iodide.

In an embodiment, the one or more silicones may include those corresponding to formula (1) wherein a=0, G=methyl, m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10; and L is —N($CH_3$)$_2$ or —$NH_2$, alternatively —$NH_2$.

Additional said at least one aminosilicone of the invention include:

(b) pendant quaternary ammonium silicones of formula (VII):

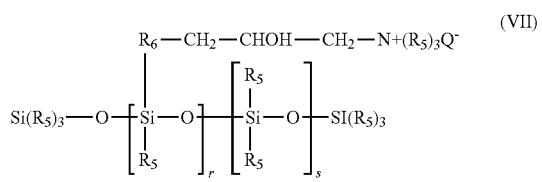

(VII)

in which:

$R_5$ is chosen from monovalent hydrocarbon-based groups comprising from 1 to 18 carbon atoms, such as $C_1$-$C_{18}$ alkyl groups and $C_2$-$C_{18}$ alkenyl groups, for example methyl;

$R_6$ is chosen from divalent hydrocarbon-based groups, such as divalent $C_1$-$C_{18}$ alkylene groups and divalent $C_1$-$C_{18}$ alkylenoxy groups, for example $C_1$-$C_8$ alkylenoxy groups, wherein said $R_6$ is bonded to the Si by way of an SiC bond;

$Q^-$ is an anion that can be for example chosen from halide ions, such as chloride, and organic acid salts (such as acetate);

r is an average statistical value ranging from 2 to 20, such as from 2 to 8;

s is an average statistical value ranging from 20 to 200, such as from 20 to 50.

Such aminosilicones are described more particularly in U.S. Pat. No. 4,185,087, the disclosure of which is incorporated by reference herein.

A silicone which falls within this class is the silicone sold by the company Union Carbide under the name "Ucar Silicone ALE 56".

Further examples of said at least one aminosilicone include:

c) quaternary ammonium silicones of formula (VIIb):

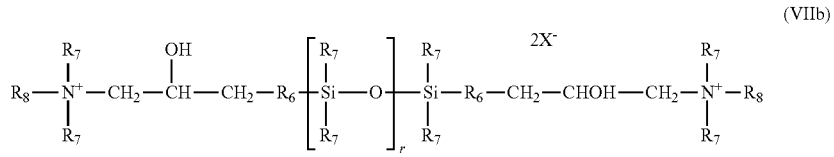

(VIIb)

in which:

groups R7, which may be identical or different, are each chosen from monovalent hydrocarbon-based groups comprising from 1 to 18 carbon atoms, such as $C_1$-$C_{18}$ alkyl groups, for example methyl, $C_2$-$C_{18}$ alkenyl groups, and rings comprising 5 or 6 carbon atoms;

R6 is chosen from divalent hydrocarbon-based groups, such as divalent C1-Cis alkylene groups and divalent $C_1$-$C_{18}$alkylenoxy, for example $C_1$-$C_8$, group connected to the Si by an SiC bond;

$R_8$, which may be identical or different, represent a hydrogen atom, a monovalent hydrocarbon-based group comprising from 1 to 18 carbon atoms, and in particular a $C_1$-$C_{18}$ alkyl group, a $C_2$-$C_{18}$ alkenyl group or a group —$R_6$—NHCOR$_7$;

$X^-$ is an anion such as a halide ion, in particular chloride, or an organic acid salt (acetate, etc.);

r represents an average statistical value from 2 to 200 and in particular from 5 to 100.

Such silicones are described, for example, in application EP-A-0 530 974, the disclosure of which is incorporated by reference herein.

Silicones falling within this class are the silicones sold by the company Eovnik under the names Abil Quat 3270, Abil Quat 3272, Abil Quat 3474 and Abil ME 45.

Further examples of said at least one aminosilicone include:

d) quaternary ammonium and polyalkylene oxide silicones wherein the quaternary nitrogen groups are located in the polysiloxane backbone, at the termini, or both.

Such silicones are described in PCT Publication No. WO 2002/010257, the disclosure of which is incorporated by reference herein.

Silicones falling within this class are the silicones sold by the company Momentive under the names Silsoft Q.

(e) Aminofunctional silicones having morpholino groups of formula (V):

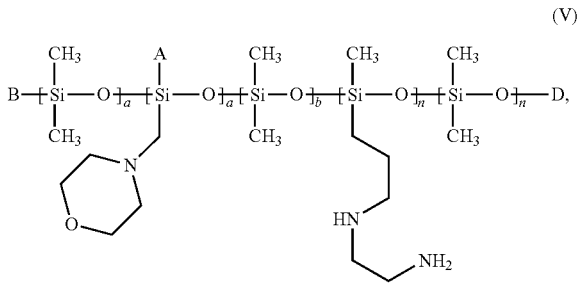
(V)

in which

A denotes a structural unit (I), (II), or (III) bound via —O—

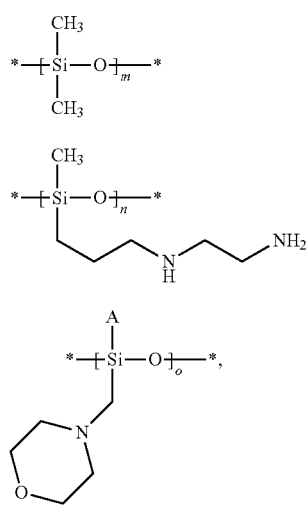

or an oligomeric or polymeric residue, bound via —O—, containing structural units of formulas (I), (II), or (III), or half of a connecting oxygen atom to a structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000.

Aminofunctional silicones of this kind bear the INCI name: Amodimethicone/Morpholinomethyl Silsesquioxane Copolymer. A particularly suitable amodimethicone is the product having the commercial name Wacker Belsil® ADM 8301E.

Examples of such silicones are available from the following suppliers:

offered by the company Dow Corning: Fluids: 2-8566, AP 6087, AP 6088, DC 8040 Fluid, fluid 8822A DC, DC 8803 & 8813 polymer, 7-6030, AP-8104, AP 8201; Emulsions: CE-8170 AF Micro Emulsion, 2-8177, 2-8194 Microemulsion, 9224 Emulsion, 939, 949, 959, DC 5-7113 Quat Microemulsion, DC 5-7070 Emulsion, DC CE-8810, CE 8401 Emulsion, CE 1619, Dow Corning Toray SS-3551, Dow Corning Toray SS-3552;

offered by the company Wacker: Wacker Belsil ADM 652, ADM 656, 1100, 1600, 1650 (fluids) ADM 6060 (linear amodimethicone) emulsion; ADM 6057 E (branched amodimethicone) emulsion; ADM 8020 VP (micro emulsion); SLM 28040 (micro emulsion);

offered by the Company Momentive: Silsoft 331, SF1708, SME 253 & 254 (emulsion), SM2125 (emulsion), SM 2658 (emulsion), Silsoft Q (emulsion)

offered by the company Shin-Etsu: KF-889, KF-8675, KF-8004, X-52-2265 (emulsion);

offered by the Company Siltech Silicones: Siltech E-2145, E-Siltech 2145-35;

offered by the company Evonik Industries: Abil T Quat 60th

Some non-limiting examples of aminosilicones include the compounds having the following INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22, Quaternium-80, as well as Silicone Quaternium-2 Panthenol Succinate and Silicone Quaternium-16/Glycidyl Dimethicone Crosspolymer.

The aminosilicones can be supplied in the form of a nanoemulsion and include MEM 9049, MEM 8177, MEM 0959, MEM 8194, SME 253, and Silsoft Q.

The one or more silicones may include dimethicones, and/or dimethiconols. The dimethiconols are hydroxyl terminated dimethylsilicones represented by the general chemical formulas

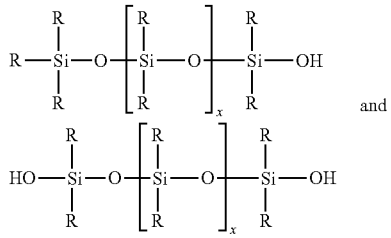

and wherein R is an alkyl group (preferably R is methyl or ethyl, more preferably methyl) and x is an integer up to about 500, chosen to achieve the desired molecular weight. Commercial dimethiconols typically are sold as mixtures with dimethicone or cyclomethicone (e.g., Dow Coming® 1401, 1402, and 1403 fluids).

2. Non-Silicone Conditioning Agents

The conditioning agent of the hair care compositions described herein may also comprise at least one organic conditioning agents, either alone or in combination with other conditioning agents, such as the silicones described above. Non-limiting examples of organic conditioning agents are described below.

a. Hydrocarbon Oils

Suitable organic conditioning agents for use as conditioning agents in hair care compositions include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils can be from about $C_{12}$ to about $C_{19}$. Branched chain hydrocarbon oils, including hydrocarbon polymers, typically will contain more than 19 carbon atoms.

b. Polyolefins

Organic conditioning oils for use in the hair care compositions described herein also include liquid polyolefins, including liquid poly-α-olefins and/or hydrogenated liquid poly-α-olefins. Polyolefins for use herein are prepared by polymerization of $C_4$ to about $C_{14}$ olefenic monomers, and in one embodiment from about $C_6$ to about $C_{12}$.

c. Fatty Esters

Other suitable organic conditioning agents for use as a conditioning agent in the hair care compositions described herein include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.). Other oligomeric or polymeric esters, prepared from unsaturated glyceryl esters can also be used as conditioning materials.

d. Fluorinated Conditioning Compounds

Fluorinated compounds suitable for delivering conditioning to hair as organic conditioning agents include perfluoropolyethers, perfluorinated olefins, fluorine based specialty polymers that may be in a fluid or elastomer form similar to the silicone fluids previously described, and perfluorinated dimethicones.

e. Fatty Alcohols

Other suitable organic conditioning oils for use in the hair care compositions described herein include, but are not limited to, fatty alcohols having at least about 10 carbon atoms, about 10 to about 22 carbon atoms, and in one embodiment about 12 to about 16 carbon atoms.

f. Alkyl Glucosides and Alkyl Glucoside Derivatives

Suitable organic conditioning oils for use in the hair care compositions described herein include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

g. Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

F. Mechanical Foam Dispenser

The mechanical foam dispenser described herein may be selected from the group consisting of squeeze foam dispensers, pump foam dispensers, other mechanical foam dispensers, and combinations thereof. In an embodiment, the mechanical foam dispenser is a squeeze foam dispenser. Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706).

The mechanical foam dispenser may comprise a reservoir for holding the hair care composition. The reservoir may be made out of any suitable material selected from the group consisting of plastic, metal, alloy, laminate, and combinations thereof. The reservoir may be a refillable reservoir such as a pour-in or screw-on reservoir, or the reservoir may be for one-time use. The reservoir may also be removable from the mechanical foam dispenser. Alternatively, the reservoir may be integrated with the mechanical foam dispenser. In an embodiment, there may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

G. Aerosol Foam Dispenser

The aerosol foam dispenser may comprise a reservoir for holding the hair care composition. The reservoir may be made out of any suitable material selected from the group consisting of plastic, metal, alloy, laminate, and combinations thereof. In an embodiment, the reservoir may be for one-time use. In an embodiment, the reservoir may be removable from the aerosol foam dispenser. Alternatively, the reservoir may be integrated with the aerosol foam dispenser. In an embodiment, there may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

H. Foaming Agent

The hair care composition described herein may comprise from about from about 1% to about 10% propellant, alternatively from about 2% to about 9% propellant, and alternatively from about 3% to about 8% propellant, by weight of the hair care composition.

The foaming agent may comprise one or more volatile materials, which in a gaseous state, may carry the other components of the hair care composition in particulate or droplet form. The foaming agent may have a boiling point within the range of from about −45° C. to about 5° C. The foaming agent may be liquefied when packaged in convention aerosol containers under pressure. The rapid boiling of the foaming agent upon leaving the aerosol foam dispenser may aid in the atomization of the other components of the hair care composition.

Aerosol foaming agent which may be employed in the hair care composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and mixtures thereof. The propellant may comprise hydrocarbons such as isobutane, propane, and butane, and these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar. The foaming agent may be hydrofluoroolefins (HFOs).

I. Viscosity

The hair care composition may have a liquid phase viscosity of from about 1 centipoise (cP) to 500 cP, alternatively from about 5 cP centipoise to about 500 cP, alternatively from about 10 cP centipoise to about 500 cP, alternatively from about 20 cP to about 500 centipoise, measured at 26.5° C. as defined herein. The viscosities are measured by a Cone and Plate Controlled Stress Brookfield Rheometer R/S Plus, by Brookfield Engineering Laboratories, Stoughton, Mass. The cone used (Spindle C-75-1) has a diameter of 75 mm and 1° angle. The viscosity is determined using a steady state flow experiment at constant shear rate of 2 s$^{-1}$ at a temperature of 26.5° C. The sample size is 2.5 ml and the total measurement reading time is 3 minutes.

J. Perfume

The hair care composition may comprise from about 0.5% to about 7%, alternatively from about 1% to about 6%, and alternatively from about 2% to about 5% perfume, by weight of the hair care composition.

The hair care composition may have a silicone to perfume ratio of from about 95:5 to about 50:50, alternatively from about 90:10 to about 60:40, and alternatively from about 85:15 to about 70:30.

Examples of suitable perfumes may be provided in the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. A plurality of perfume components may be present in the hair care composition.

K. Optional Ingredients

The hair conditioning composition described herein may optionally comprise one or more additional components known for use in hair care or personal care products, provided that the additional components are physically and chemically compatible with the essential components described herein, or do not otherwise unduly impair product stability, aesthetics or performance Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the conditioning composition.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, cationic polymers, viscosity modifiers, coloring agents or dyes, conditioning agents, hair bleaching agents, thickeners, moisturizers, foam boosters, additional surfactants or nonionic cosurfactants, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, non-volatile solvents or diluents (water-soluble and water-insoluble), co-solvents or other additional solvents, and similar other materials.

Non-limiting examples of anti-dandruff agents include one material or a mixture selected from the groups consisting of: azoles, such as climbazole, ketoconazole, itraconazole, econazole, and elubiol; hydroxyl pyridones, such as octopirox (piroctone olamine), ciclopirox, rilopirox, and MEA-Hydroxyoctyloxypyridinone; kerolytic agents, such as salicylic acid and other hydroxy acids; strobilurins such as azoxystrobin and metal chelators such as 1,10-phenanthroline. In another embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, 10 flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. In an embodiment, the azole anti-microbial active is ketoconazole. In an embodiment, the sole antimicrobial active is ketoconazole.

Method of Treating Hair

The method of treating the hair described herein comprises (1) providing a hair care composition, as described herein, (2) dispensing the hair care composition as a liquid form or a foam form using a mechanical foam dispenser or an aerosol foam dispenser; (3) applying the composition to the hair; and (4) rinsing the composition from the hair. The hair care composition can form a stable foam. A foam is stable when it substantially sustains its volume from the time of dispensing to its application on hair. The foam can have a density of from about 0.03 g/mL to about 0.35 g/mL when dispensed from the aerosol foam dispenser. The foam can also have a foam density of from about 0.05 g/cm3 to about 0.35 g/cm3, alternatively from about 0.08 g/cm3 to about 0.25 g/cm3, alternatively from about 0.08 g/cm3 to about 0.2 g/cm3, alternatively from about 0.08 g/cm3 to about 0.18 g/cm3, alternatively from about 0.08 g/cm3 to about 0.15 g/cm3, alternatively from about 0.08 g/cm3 to about 0.12 g/cm3; alternatively from about 0.1 g/cm3 to about 0.12 g/cm3, alternatively from about 0.12 g/cm3 to about 0.2 g/cm3, or alternatively from about 0.15 g/cm3 to about 0.2 g/cm3.

Method of Foam Density Determination

Foam density is measured by placing a 100 ml beaker onto a mass balance, tarring the mass of the beaker and then dispensing product from the aerosol container into the 100 ml beaker until the volume of the foam is above the rim of the vessel. The foam is made level with the top of the beaker by scraping a spatula across it. The resulting mass of the 100 ml of foam is then divided by the volume (100) to determine the foam density in units of g/ml.

EXAMPLES

The following examples illustrate the hair care composition described herein. The exemplified compositions can be prepared by conventional formulation and mixing techniques. It will be appreciated that other modifications of the present invention within the skill of those in the hair care formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following are non-limiting examples of the hair care composition described herein.

Examples and Results

Compact, clear hair care compositions having low viscosity

| | Ex. 1 | Ex. 2 | Ex. 3 | Ex. 4 | Ex. 5 |
|---|---|---|---|---|---|
| Linear Sodium laureth-1-sulfate SLE1S[1] | 8 | 8 | 13 | 8 | 4 |
| Branched sodium trideceth-2-sulfate ST2S[2] | 18 | 16 | 13 | 18 | 22 |
| Cocamidopropyl betaine[3] | 4 | 6 | 4 | 4 | 4 |
| perfume | 2.4 | 2.4 | 2.4 | 2.4 | 2.4 |
| Dipropylene glycol | 4 | 4 | 8 | 8 | 8 |
| Preservatives, pH adjusters | Up to 1% | Up to 1% | Up to 1% | Up to 1% | Up to 1% |
| Water | Q.S. | Q.S. | Q.S. | Q.S. | Q.S. |
| SLE1S/ST2S | 0.44 | 0.50 | 1.00 | 0.44 | 0.18 |
| Total Anionic Surfactant | 26 | 24 | 26 | 26 | 26 |
| Chain length % < C12 | <5 | <5 | <5 | <5 | <5 |
| Chain Length % > or = C12 | >95 | >95 | >95 | >95 | >95 |
| Total Branching % | 69.2 | 66.7 | 50.0 | 69.2 | 84.6 |
| EO % | 1.87 | 1.69 | 1.60 | 1.87 | 2.08 |
| Viscosity | 435 | 341 | 329 | 232 | 165 |
| Stability | Stable | Stable | Stable | Stable | Stable |
| SLE1S/(ST2S* Solvent) | 0.11 | 0.13 | 0.13 | 0.06 | 0.02 |
| ST2S/Solvent | 4.50 | 4.00 | 1.63 | 2.25 | 2.75 |
| Total surfactant | 30 | 30 | 30 | 30 | 30 |

| | Ex. 6 | Ex. 7 | Ex. 8 | Ex. 9 | Ex. 10 |
|---|---|---|---|---|---|
| Linear Sodium laureth-1-sulfate SLE1S[1] | 0 | 12 | 8 | 4 | 0 |
| Branched sodium trideceth-2-sulfate ST2S[2] | 26 | 12 | 16 | 20 | 24 |
| Cocamidopropyl betaine[3] | 4 | 6 | 6 | 6 | 6 |
| perfume | 2.4 | 2.4 | 2.4 | 2.4 | 2.4 |
| Dipropylene glycol | 8 | 8 | 8 | 8 | 8 |
| Preservatives, pH adjusters | Up to 1% | Up to 1% | Up to 1% | Up to 1% | Up to 1% |
| Water | Q.S. | Q.S. | Q.S. | Q.S. | Q.S. |
| SLE1S/ST2S | 0.00 | 1.00 | 0.50 | 0.20 | 0.00 |
| Total Anionic Surfactant | 26 | 24 | 24 | 24 | 24 |
| Chain length % < C12 | <5 | <5 | <5 | <5 | <5 |
| Chain Length % > or = C12 | >95 | >95 | >95 | >95 | >95 |
| Total Branching % | 100.0 | 50.0 | 66.7 | 83.3 | 100.0 |
| EO % | 2.29 | 1.48 | 1.69 | 1.90 | 2.11 |
| Viscosity | 122 | 368 | 242 | 172 | 120 |
| Stability | Stable | Stable | Stable | Stable | Stable |
| SLE1S/(ST2S* Solvent) | 0.00 | 0.13 | 0.06 | 0.03 | 0.00 |
| ST2S/Solvent | 3.25 | 1.50 | 2.00 | 2.50 | 3.00 |
| Total surfactant | 30 | 30 | 30 | 30 | 30 |

| | Ex. 11 | Ex. 12 | Ex. 13 | Ex. 14 | Ex. 15 |
|---|---|---|---|---|---|
| Linear Sodium laureth-1-sulfate SLE1S[1] | 15 | 10 | 11 | 10 | 12 |
| Branched sodium trideceth-2-sulfate ST2S[2] | 15 | 20 | 11 | 10 | 8 |
| Cocamidopropyl betaine[3] | | | 8 | 10 | 10 |
| perfume | 2.4 | 2.4 | 2.4 | 2.4 | 2.4 |
| Dipropylene glycol | 8 | 8 | 8 | 8 | 8 |
| Preservatives, pH adjusters | Up to 1% | Up to 1% | Up to 1% | Up to 1% | Up to 1% |
| Water | Q.S. | Q.S. | Q.S. | Q.S. | Q.S. |
| SLE1S/ST2S | 1.00 | 0.50 | 1.00 | 1.00 | 1.50 |
| Total Anionic Surfactant | 30 | 30 | 22 | 20 | 20 |
| Chain length % < C12 | <5 | <5 | <5 | <5 | <5 |
| Chain Length % > or = C12 | >95 | >95 | >95 | >95 | >95 |
| Total Branching % | 50.0 | 66.7 | 50.0 | 50.0 | 40.0 |
| EO % | 1.85 | 2.11 | 1.36 | 1.23 | 1.13 |
| Viscosity | 271 | 232 | 262 | 307 | 470 |
| Stability | Stable | Stable | Stable | Stable | Stable |
| SLE1S/(ST2S* Solvent) | 0.13 | 0.06 | 0.13 | 0.13 | 0.19 |
| ST2S/Solvent | 1.88 | 2.50 | 1.38 | 1.25 | 1.00 |

| | Ex. 16 | Ex. 17 | Ex. 18 | Ex. 19 |
|---|---|---|---|---|
| Linear Sodium laureth-1-sulfate SLE1S[1] | 15 | 10 | 11 | 4 |
| Branched sodium trideceth-2-sulfate ST2S[2] | 15 | 20 | 11 | 22 |

-continued

|  |  |  |  |  |
|---|---|---|---|---|
| Cocamidopropyl betaine[3] |  |  | 8 | 4 |
| perfume | 2.4 | 2.4 | 2.4 | 2.4 |
| Dipropylene glycol | 8 | 8 | 8 | 8 |
| Piroctone Olarnine[4] | 1 | 1 | 1 | 1 |
| Preservatives, pH adjusters | Up to 1% | Up to 1% | Up to 1% | Up to 1% |
| Water | Q.S. | Q.S. | Q.S. | Q.S. |
| SLE1S/ST2S | 1.00 | 0.50 | 1.00 | 0.18 |
| Total Anionic Surfactant | 30 | 30 | 22 | 26 |
| Chain length % < C12 | <5 | <5 | <5 | <5 |
| Chain Length % > or = C12 | >95 | >95 | >95 | >95 |
| Total Branching % | 50.0 | 66.7 | 50.0 | 84.6 |
| EO % | 1.85 | 2.11 | 1.36 | 2.08 |
| Viscosity | 280 | 240 | 270 | 175 |
| Stability | Stable | Stable | Stable | Stable |
| SLE1S/(ST2S* Solvent) | 0.13 | 0.06 | 0.13 | 0.02 |
| ST2S/Solvent | 1.88 | 2.50 | 1.38 | 2.75 |

Comparative Examples

|  | Comp. Ex. 1 | Comp. Ex. 2 | Comp. Ex. 3 | Comp. Ex. 4 | Comp. Ex. 5 |
|---|---|---|---|---|---|
| Linear Sodium laureth-1-sulfate SLE1S[1] | 15 | 15 | 11 | 12 | 13 |
| Branched sodium trideceth-2-sulfate ST2S[2] | 15 | 15 | 11 | 12 | 13 |
| Cocamidopropyl betaine[3] |  |  | 8 | 6 | 4 |
| perfume | 2.4 | 1.6 | 2.4 | 2.4 | 2.4 |
| Dipropylene glycol | 4 | 4 | 4 | 4 | 4 |
| Preservatives, pH adjusters | Up to 1% | Up to 1% | Up to 1% | Up to 1% | Up to 1% |
| Water | Q.S. | Q.S. | Q.S. | Q.S. | Q.S. |
| SLE1S/ST2S | 1.00 | 1.00 | 1.00 | 1.00 | 1.00 |
| Total Anionic Surfactant | 30 | 30 | 22 | 24 | 26 |
| Chain length % < C12 | <5 | <5 | <5 | <5 | <5 |
| Chain Length % > or = C12 | >95 | >95 | >95 | >95 | >95 |
| Total Branching % | 50.0 | 50.0 | 50.0 | 50.0 | 50.0 |
| EO % | 1.85 | 1.85 | 1.36 | 1.48 | 1.60 |
| Viscosity | 11902 | 7537 | 611 | 717 | 961 |
| Stability | Stable | Stable | Stable | Stable | Stable |
| SLE1S/(ST2S* Solvent) | 0.25 | 0.25 | 0.25 | 0.25 | 0.25 |
| ST2S/Solvent | 3.75 | 3.75 | 2.75 | 3.00 | 3.25 |
| Total surfactant | 30 | 30 | 30 | 30 | 30 |

|  | Comp. Ex. 6 | Comp. Ex. 7 | Comp. Ex. 8 | Comp. Ex. 9 | Comp. Ex. 10 |
|---|---|---|---|---|---|
| Linear Sodium laureth-1-sulfate SLE1S[1] | 12 | 26 | 22 | 18 | 24 |
| Branched sodium trideceth-2-sulfate ST2S[2] | 8 | 0 | 4 | 8 | 0 |
| Cocamidopropyl betaine[3] | 10 | 4 | 4 | 4 | 6 |
| perfume | 2.4 | 2.4 | 2.4 | 2.4 | 2.4 |
| Dipropylene glycol | 4 | 8 | 8 | 8 | 8 |
| Preservatives, pH adjusters | Up to 1% | Up to 1% | Up to 1% | Up to 1% | Up to 1% |
| Water | Q.S. | Q.S. | Q.S. | Q.S. | Q.S. |
| SLE1S/ST2S | 1.50 | High | 5.50 | 2.25 | High |
| Total Anionic Surfactant | 20 | 26 | 26 | 26 | 24 |
| Chain length % < C12 | <5 | <5 | <5 | <5 | <5 |
| Chain Length % > or = C12 | >95 | >95 | >95 | >95 | >95 |
| Total Branching % | 40.0 | 0.0 | 15.4 | 30.8 | 0.0 |
| EO % | 1.13 | 0.92 | 1.13 | 1.34 | 0.85 |
| Viscosity | 751 | 1112 | 915 | 579 | 1456 |
| Stability | Stable | Stable | Stable | Stable | Stable |
| SLE1S/(ST2S* Solvent) | 0.38 | High | 0.69 | 0.28 | High |
| ST2S/Solvent | 2.00 | 0.00 | 0.50 | 1.00 | 0.00 |
| Total surfactant | 30 | 30 | 30 | 30 | 30 |

|  | Comp. Ex. 11 | Comp. Ex. 12 | Comp. Ex. 13 | Comp. Ex. 14 | Comp. Ex. 15 |
|---|---|---|---|---|---|
| Linear Sodium laureth-1-sulfate SLE1S[1] | 20 | 16 | 15 | 15 | 18 |
| Branched sodium trideceth-2-sulfate ST2S[2] | 4 | 8 | 15 | 15 | 8 |

| | | | | | |
|---|---|---|---|---|---|
| Cocamidopropyl betaine[3] | 6 | 6 | | | 4 |
| perfume | 2.4 | 2.4 | 2.4 | 1.6 | 2.4 |
| Dipropylene glycol | 8 | 8 | 4 | 4 | 4 |
| Preservatives, pH adjusters | Up to 1% | Up to 1% | Up to 1% | Up to 1% | Up to 1% |
| Water | Q.S. | Q.S. | Q.S. | Q.S. | Q.S. |
| SLE1S/ST2S | 5.00 | 2.00 | 1.00 | 1.00 | 2.25 |
| Total Anionic Surfactant | 24 | 24 | 30 | 30 | 26 |
| Chain length % < C12 | <5 | <5 | <5 | <5 | <5 |
| Chain Length % > or = C12 | >95 | >95 | >95 | >95 | >95 |
| Total Branching % | 16.7 | 33.3 | 50.0 | 50.0 | 30.8 |
| EO % | 1.06 | 1.27 | 1.85 | 1.85 | 1.34 |
| Viscosity | 803 | 596 | 11902 | 7537 | 2324 |
| Stability | Stable | Stable | Stable | Stable | Stable |
| SLE1S/(ST2S* Solvent) | 0.63 | 0.25 | 0.25 | 0.25 | 0.56 |
| ST2S/Solvent | 0.50 | 1.00 | 3.75 | 3.75 | 2.00 |
| Total surfactant | 30 | 30 | 30 | 30 | 30 |

| | Comp. Ex. 16 | Comp. Ex. 17 | Comp. Ex. 18 | Comp. Ex. 19 | Comp. Ex. 20 |
|---|---|---|---|---|---|
| Linear Sodium laureth-1-sulfate SLE1S[1] | 16 | 16 | 14 | 30 | 0 |
| Branched sodium trideceth-2-sulfate ST2S[2] | 4 | 8 | 8 | 0 | 30 |
| Cocamidopropyl betaine[3] | 10 | 6 | 8 | 0 | 0 |
| perfume | 2.4 | 2.4 | 2.4 | 2.4 | 2.4 |
| Dipropylene glycol | 4 | 4 | 4 | | |
| Preservatives, pH adjusters | Up to 1% | Up to 1% | Up to 1% | Up to 1% | Up to 1% |
| Water | Q.S. | Q.S. | Q.S. | Q.S. | Q.S. |
| SLE1S/ST2S | 4.00 | 2.00 | 1.75 | High | 0.00 |
| Total Anionic Surfactant | 20 | 24 | 22 | 30 | 30 |
| Chain length % < C12 | <5 | <5 | <5 | <5 | <5 |
| Chain Length % > or = C12 | >95 | >95 | >95 | >95 | >95 |
| Total Branching % | 20.0 | 33.3 | 36.4 | 0.0 | 100.0 |
| EO % | 0.92 | 1.27 | 1.20 | 1.06 | 2.64 |
| Viscosity | 1832 | 1481 | 1110 | 118664 | |
| Stability | Stable | Stable | Stable | Stable | Unstable |
| SLE1S/(ST2S* Solvent) | 1.00 | 0.50 | 0.44 | High | High |
| ST2S/Solvent | 1.00 | 2.00 | 2.00 | High | High |
| Total surfactant | 30 | 30 | 30 | 30 | 30 |

| | Comp. Ex. 21 | Comp. Ex. 22 | Comp. Ex. 23 |
|---|---|---|---|
| Linear Sodium laureth-1-sulfate SLE1S[1] | 22 | 4 | 0 |
| Branched sodium trideceth-2-sulfate ST2S[2] | 4 | 22 | 26 |
| Cocamidopropyl betaine[3] | 4 | 4 | 4 |
| perfume | 2.4 | 2.4 | 2.4 |
| Dipropylene glycol | 4 | 4 | 4 |
| Preservatives, pH adjusters | Up to 1% | Up to 1% | Up to 1% |
| Water | Q.S. | Q.S. | Q.S. |
| SLE1S/ST2S | 5.50 | 0.18 | 0.00 |
| Total Anionic Surfactant | 26 | 26 | 26 |
| Chain length % < C12 | <5 | <5 | <5 |
| Chain Length % > or = C12 | >95 | >95 | >95 |
| Total Branching % | 15.4 | 84.6 | 100.0 |
| EO % | 1.13 | 2.08 | 2.29 |
| Viscosity | 4627 | | |
| Stability | | Unstable | Unstable |
| SLE1S/(ST2S* Solvent) | 1.38 | 0.05 | 0.00 |
| ST2S/Solvent | 1.00 | 5.50 | 6.50 |
| Total surfactant | 30 | 30 | 30 |

1. Sodium Laureth (1 molar ethylene oxide) sulfate at 70% active, supplier: Stephan Co
2. Sodium Tridecyl Ether Sulfate (2 molar ethylene oxide), Stepan ST2S-65 (Steol-TD 40265) 65% active, supplier: Stephan Co
3. Amphosol HCA from Stepan Company
4. Octopirox (Piroctone Olamine) from Clariant Paragraph A. A stable concentrated hair care composition comprising:
a) from about 20 weight % to about 45 weight % total surfactant;
c) from about 6 weight % to about 30 weight % branched anionic surfactant with a tail having an alkyl chain with 12 to 18 carbon atoms;
d) from about 0.1% weight % to about 20 weight % linear anionic surfactant with a tail having an alkyl chain with 12 to 18 carbon atom;
e) from about 2 weight % to about 12 weight % water-miscible solvent; and
f) from about 35 weight % to about 78 weight % of water; wherein the concentrated hair care has Ratio of (Linear anionic surfactant/Branched anionic surfactant)/Miscible solvent of less than about 0.2 and wherein the ratio of branched anionic surfactant/miscible solvent is less than about 5 and wherein the concentrated hair care has a viscosity of from about 5 to about 500 cP at 26.5° C.

Paragraph B. The hair care composition of Paragraph A, having viscosity of about 1 to about 500 cP at 26.5° C.

Paragraph C. The hair care composition of Paragraph A-B, wherein the composition further comprises from about 0.1 weight % to about 10 weight % amphoteric surfactant.

Paragraph D. The hair care composition of Paragraph A-C, wherein the hair care composition further contains about 0.05 to 5 weight percent of a silicone conditioning agent.

Paragraph E. The hair care composition of Paragraph A-D, wherein the silicone conditioning agent contains one of more quaternary ammonium salt in its molecular structure.

Paragraph F. The hair care composition of Paragraph A-E, wherein the silicone conditioning agent is dimethiconol micro-emulsion.

Paragraph G. The hair care composition of Paragraph A-F, wherein the hair care composition further comprises from about 0.05 to about 2 weight % of the hair care composition of one or more cationic polymers.

Paragraph H. The hair care composition of Paragraph A-G, wherein the concentration of the cationic polymer is from about 0.05 to about 1 weight % of the composition.

Paragraph I. The hair care composition of Paragraph A-H, wherein the cationic polymers are selected from the group consisting of guar hydroxylpropyltrimonium chloride, Polyquaternium-6, Polyquaternium-7, Polyquaternium-10, Polyquaternium-39, Polyquaterinum-67, and mixtures thereof.

Paragraph J. The hair care composition of Paragraph A-I, wherein the guar hydroxylpropyltrimonium chloride has a weight average molecular weight of less than about 1.0 million g/mol.

Paragraph K. The hair care composition of Paragraph A-J, wherein the guar hydroxylpropyltrimonium chloride has a weight average molecular weight of less than about 800,000 g/mol.

Paragraph L. The hair care composition of Paragraph A-K, wherein the guar hydroxylpropyltrimonium chloride has a weight average molecular weight of from about 100,000 to about 900,000 g/m.

Paragraph M. The hair care composition of Paragraph A-L, wherein the total surfactant level is from about 20% to about 45% by weight.

Paragraph N. The hair care composition of Paragraph A-M, wherein the total surfactant level is from about 25% to about 35% by weight.

Paragraph O. The hair care composition of Paragraph A-N, wherein the branched anionic surfactant is selected from the group consisting of sodium trideceth sulfate, sodium tridecyl sulfate, sodium C12-13 alkyl sulfate, sodium C12-15 alkyl sulfate, sodium C12-18 alkyl sulfate, sodium C12-13 pareth sulfate, sodium C12-13 pareth-n sulfate, sodium C12-14 pareth-n sulfate, and combinations thereof.

Paragraph P. The hair care composition of Paragraph A-O, wherein the linear anionic surfactant is selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth-1 sulfate, sulfate, sodium trideceth-2 sulfate, sulfate, sodium trideceth-3 sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

Paragraph Q. The hair care composition of Paragraph A-P, wherein the hair care composition further comprises about 0.5 to 7 weight percent of a perfume.

Paragraph R. A stable concentrated hair care composition comprising:

a) from about 20 weight % to about 45 weight % total surfactant;

b) from about 6 weight % to about 30 weight % branched anionic surfactant with a tail having an alkyl chain with 12 carbon atoms or higher;

c) from about 2 weight % to about 12 weight % water-miscible solvent; and d) from about 35 weight % to about 78 weight % of water;

and wherein the ratio of branched anionic surfactant/miscible solvent is less than about 5 and wherein the concentrated hair care has a viscosity of less than 500 cP at 26.5° C. and wherein the composition has about 0 weight % linear anionic surfactant with tail having an alkyl chain with 12 to 18 carbon atoms.

Paragraph S. The hair care composition of Paragraph A-R, wherein the composition has a viscosity of about 10 to about 500 cP at 26.5° C.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A stable concentrated hair care composition comprising:
   a) from about 20 weight % to about 45 weight % total surfactant;
   b) from about 6 weight % to about 30 weight % branched anionic surfactant with a tail having an alkyl chain with 12 to 18 carbon atoms;
   c) from about 4 weight % to about 15 weight % linear anionic surfactant with a tail having an alkyl chain with 12 to 18 carbon atom;
   d) from about 2 weight % to about 12 weight % water-miscible solvent;
   e) from about 0.05% to about 1% of a cationic polymer; and
   f) from about 35 weight % to about 78 weight % of water;
   wherein the concentrated hair care composition is a shampoo, has a Ratio of (Linear anionic surfactant/Branched anionic surfactant)/Miscible solvent of less than about 0.2, a ratio of branched anionic surfactant/miscible solvent of less than about 5, and a viscosity of less than 500 cP at 26.5° C.

2. The hair care composition of claim 1, having viscosity of about 1 to about 500 cP at 26.5° C.

3. The hair care composition of claim 1, wherein the composition has a viscosity of about 5 to about 500 cP at 26.5° C.

4. The hair care composition of claim 1, wherein the composition has a viscosity of about 10 to about 500 cP at 26.5° C.

5. The hair care composition of claim 1, wherein the composition further comprises from about 0.1 weight % to about 10 weight % amphoteric surfactant.

6. The hair care composition of claim 1, wherein the hair care composition further contains about 0.05 to 5 weight percent of a silicone conditioning agent.

7. The hair care composition of claim 6, wherein the silicone conditioning agent contains one or more quaternary ammonium salts in its molecular structure.

8. The hair care composition of claim 6, wherein the silicone conditioning agent is dimethiconol micro-emulsion.

9. The hair care composition of claim 1, wherein the composition further comprises from about 0.1 weight % to about 5 weight % of one or more anti-dandruff active.

10. The hair care composition of claim 9, wherein the anti-dandruff active is selected from the group consisting of piroctone olamine, climbazole, and salicylic acid and mixtures thereof.

11. The hair care composition of claim 1, wherein the cationic polymers are selected from the group consisting of guar hydroxylpropyltrimonium chloride, Polyquaternium-6, Polyquaternium-7, Polyquaternium-10, Polyquaternium-39, Polyquaterinum-67, and mixtures thereof.

12. The hair care composition of claim 11, wherein the guar hydroxylpropyltrimonium chloride has a weight average molecular weight of from about 100,000 to about 2,000,000 g/m and a charge density of from about 0.2 to about 2.2 meg/g.

13. The hair care composition of claim 1, wherein the total surfactant level is from about 25% to about 35% by weight.

14. The hair care composition of claim 1, wherein the branched anionic surfactant is selected from the group consisting of branched sodium trideceth sulfate, branched sodium tridecyl sulfate, branched sodium C12-13 alkyl sulfate, branched sodium C12-15 alkyl sulfate, branched sodium C12-18 alkyl sulfate, branched sodium C12-13 pareth sulfate, branched sodium C12-13 pareth-n sulfate, branched sodium C12-14 pareth-n sulfate, and combinations thereof.

15. The hair care composition of claim 1, wherein the linear anionic surfactant is selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth-1 sulfate, sulfate, sodium trideceth-2 sulfate, sulfate, sodium trideceth-3 sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

16. The hair care composition of claim 1, wherein the linear anionic surfactant is selected from the group consisting of acyl isethionate, acyl methyl isethionate, acyl glutamate, acyl glycinate, acyl sarcosinate, acyl alaninate, acyl taurate, sulfosuccinate, alkyl benzene sulfonate, alkyl ether carboxylate, alkylamphoacetate, alpha olefin sulfonate, sodium cocoyl isethionate, sodium lauroyl isethionate, sodium lauroyl methyl isethionate, sodium cocoyl glutamate, disodium cocoyl glutamate, sodium lauroyl glutamate, disodium lauroyl glutamate, sodium cocoyl alaninate, sodium lauroyl alaninate, sodium lauroyl glycinate, sodium cocoyl glycinate, sodium laureth sulfosuccinate, disodium laureth sulfosuccinate, disodium lauryl sulfosuccinate, sodium lauryl glucose carboxylate, sodium cocoyl glucose carboxylate, sodium cocoyl amphoacetate, sodium lauroyl amphoacetate, sodium methyl cocoyl taurate, and mixtures thereof.

17. The hair care composition of claim 1, wherein the hair care composition further comprises about 0.5 to 7 weight percent of a perfume.

* * * * *